(12) United States Patent
Okunishi et al.

(10) Patent No.: US 11,839,637 B2
(45) Date of Patent: *Dec. 12, 2023

(54) NEURON ACTIVATOR

(71) Applicant: Kinjirushi Co., Ltd., Nagoya (JP)

(72) Inventors: Isao Okunishi, Nagoya (JP); Tomoe Kato, Nagoya (JP)

(73) Assignee: Kinjirushi Co., Ltd., Nagoya (JP)

( * ) Notice: Subject to any disclaimer, the term of this patent is extended or adjusted under 35 U.S.C. 154(b) by 160 days.

This patent is subject to a terminal disclaimer.

(21) Appl. No.: 17/344,609

(22) Filed: Jun. 10, 2021

(65) Prior Publication Data

US 2021/0299199 A1 Sep. 30, 2021

Related U.S. Application Data

(63) Continuation of application No. 16/144,641, filed on Sep. 27, 2018, now Pat. No. 11,065,288.

(30) Foreign Application Priority Data

| Sep. 29, 2017 | (JP) | 2017-191583 |
|---|---|---|
| Sep. 29, 2017 | (JP) | 2017-191584 |
| Sep. 29, 2017 | (JP) | 2017-191585 |

(51) Int. Cl.

| *A61K 36/16* | (2006.01) |
| *A61K 36/9066* | (2006.01) |
| *A61P 25/28* | (2006.01) |
| *A61K 31/05* | (2006.01) |
| *A61K 31/26* | (2006.01) |
| *A23L 33/12* | (2016.01) |
| *A23L 33/105* | (2016.01) |
| *A23L 33/115* | (2016.01) |
| *A61K 35/00* | (2006.01) |

(52) U.S. Cl.
CPC .......... *A61K 36/16* (2013.01); *A23L 33/105* (2016.08); *A23L 33/115* (2016.08); *A23L 33/12* (2016.08); *A61K 31/05* (2013.01); *A61K 31/26* (2013.01); *A61K 35/00* (2013.01); *A61K 36/9066* (2013.01); *A61P 25/28* (2018.01); *A23V 2002/00* (2013.01)

(58) Field of Classification Search
None
See application file for complete search history.

(56) References Cited

U.S. PATENT DOCUMENTS

| 2003/0064131 A1 | 4/2003 | Murata et al. |
| 2005/0239882 A1 | 10/2005 | Kim |
| 2007/0032548 A1 | 2/2007 | Ellis |
| 2009/0123575 A1 | 5/2009 | Lake et al. |
| 2011/0280852 A1 | 11/2011 | Miller |
| 2013/0079401 A1 | 3/2013 | Chen |
| 2015/0023922 A1 | 1/2015 | Kuang et al. |
| 2016/0151320 A1 | 6/2016 | Domingo Pedro et al. |
| 2017/0049842 A1 | 2/2017 | Furuya et al. |

FOREIGN PATENT DOCUMENTS

| CN | 101366709 A | 2/2009 |
| CN | 105431056 A | 3/2016 |
| JP | 2001-064253 A | 3/2001 |
| JP | 2006-016362 A | 1/2006 |
| JP | 2006321737 A | 11/2006 |
| JP | 3919489 B2 | 5/2007 |
| JP | 2008019242 A | 1/2008 |
| JP | 2008-247805 A | 10/2008 |
| JP | 2010202559 A | 9/2010 |
| JP | 2013526865 A | 6/2013 |
| JP | 2014-028830 A | 2/2014 |
| JP | 2015107960 A | 6/2015 |
| JP | 2015147775 A | 8/2015 |
| JP | 2015051927 A | 9/2015 |
| JP | 2015208282 A | 11/2015 |

OTHER PUBLICATIONS

Shibata, T., et al. "A food-derived synergist of NGF signaling: identification of protein tyrosine phosphatase 1B as a key regulator of NGF receptor-initiated signal transduction", Journal of Neurochemistry, 2008, 107, 1248-1260.

Cao, D., et al. "Effects of docosahexaenoic acid on the survival and neurite outgrowth of rat cortical neurons in primary cultures", Journal of Nutritional Biochemistry 16, 2005, 538-546.

Morroni, F., et al. "Neuroprotection by 6-(methylsulfinyl)hexyl isothiocyanate in a 6-hydroxydopamine mouse model of Parkinson's disease", Brain Research 1589, 2014, 93-104.

Cheung, K.L. et al. "Synergistic Effect of Combination of Phenethyl Isothiocyanate and Sulforaphane or Curcumin and Sulforaphane in the Inhibition of Inflammation", Pharmaceutical Research, vol. 26, No. 1, Jan. 2009, 224-231.

Xu, S.L., et al. "Isorhamnetin, A Flavonol Aglycone from *Ginkgo biloba* L., Induces Neuronal Differentiation of Cultured PC12 Cells: Potentiating the Effect of Nerve Growth Factor", Hindawi Publishing Corporation, Evidence-Based Complementary and Alternative Medicine, vol. 2012, Article ID 278273, 11 pages.

Dikshit, P., et al. "Curcumin Induces Stress Response, Neurite Outgrowth and Prevent NF-κB Activation by Inhibiting the Proteasome Function", Neurotoxicity Research, 2006, vol. 9(1). 29-37.

(Continued)

*Primary Examiner* — Russell G Fiebig
(74) *Attorney, Agent, or Firm* — Westman, Champlin & Koehler, P.A.; Z. Peter Sawicki; Amanda M. Prose

(57) ABSTRACT

The present disclosure provides a neuron activator that activates neurons. The neuron activator includes at least one selected from the group consisting of a dopamine production promotor that promotes dopamine production of the neurons, a neuron extension promotor that promotes extension of the neurons, and an amyloid β resistance enhancer that enhances resistance of the neurons against amyloid β. The neuron activator includes 6-methylsulfinylhexyl isothiocyanates or glycosides thereof, and at least one selected from the group consisting of unsaturated fatty acid and polyphenol.

8 Claims, 9 Drawing Sheets

(56) References Cited

OTHER PUBLICATIONS

Watanabe, M. et al. "Identification of 6-methylsulfinylhexyl isothiocyanate as an apoptosis-inducing component in wasabi" Phytochemistry 62 (2003) 733-739.
Bisht, S. et al. "Polymeric nanoparticle-encapsulated curcumin ("nanocurcumin"): a novel strategy for human cancer therapy" Journal of Nanobiotechnology 2007, 5:3.
Fasano, E. et al. "DHA induces apoptosis by altering the expression and cellular location of GRP78 in colon cancer cell lines" Biochimica et Biophysica Acta 1822 (2012) 1762-1772.
Lee, H.-J. et al. "Mitochondria-cytochrome C-caspase-9 cascade mediates isorhamnetin-induced apoptosis" Cancer Letters 270 (2008) 342-353.
Merendino, N. et al. "Dietary ω-3 Polyunsaturated Fatty Acid DHA: A Potential Adjuvant in the Treatment of Cancer" BioMed Research International, Hindawi Publishing Corporation, 2013, Article ID 310186, 11 pages.
Mukerjee, A. et al. "Formulation, Characterization and Evaluation of Curcumin-loaded PLGA Nanospheres for Cancer Therapy" Anticancer Research (2009) 29:3867-3876.
Zhang, Y. et al. "Ginkgo biloba Extract Kaempferol Inhibits Cell Proliferation and Induces Apoptosis in Pancreatic Cancer Cells" Journal of Surgical Research (2008) 148, 17-23.
Office Action in the counterpart Chinese Application No. 201811140138.6 dated Sep. 17, 2020 and its machine English translation.
Office Action in the counterpart Chinese Application No. 201811140138.6 dated Feb. 26, 2021 and its machine English translation.
Notice of Reasons for Refusal issued in the priority application, JP 2017-191583, dated Jun. 8, 2021.
Notice of Reasons for Refusal issued in the priority application, JP 2017-191584, dated Jun. 8, 2021.
Notice of Reasons for Refusal issued in the priority application, JP 2017-191585, dated Jun. 8, 2021.
Echeverry, C., et al. "Pretreatment with Natural Flavones and Neuronal Cell Survival after Oxidative Stress: A Structure—Activity Relationship Study" J. Agric. Food Chem., 2010, vol. 58, pp. 2111-2115.
Iida, A., et al. "Protective effects of Nitraria retusa extract and its constituent isorhamnetin against amyloid ß-induced cytotoxicity and amyloid ß aggregation" Bioscience, Biotechnology, and Biochemistry, 2015, vol. 79, No. 9, pp. 1548-1551.
Notice of Reasons for Rejection issued for Chinese patent application serial No. 201811140138.6, dated Sep. 16, 2021, with machine English translation.

NEURON ACTIVATOR

CROSS-REFERENCE TO RELATED APPLICATIONS

This application is a continuation of U.S. patent application Ser. No. 16/144,641, filed Sep. 27, 2018, which claims the benefit of Japanese Patent Application Nos. 2017-191584, 2017-191585, and 2017-191583 all filed on Sep. 29, 2017 with the Japan Patent Office, the entire disclosures of which are incorporated herein by reference.

BACKGROUND

The present disclosure relates to a neuron activator that activates neurons.

In recent years, researches on dementia have progressed in preparation for an aging society. Parkinson's disease is one of dementia. Parkinson's disease progresses by degeneration and shedding of dopaminergic neuron, resulting in decrease in dopamine-producing ability of neurons.

Therefore, conventionally, various measures have been taken for inhibiting the decrease in dopamine-producing ability of neurons or promoting the production, for example, as disclosed in Japanese Unexamined Patent Application Publication Nos. 2006-321737, 2008-19242, and 2015-208282.

The inventors of the present application have made extensive exploration for substances that are different from those of the prior art and that promote dopamine-producing ability of neurons.

Also, various causes are known for an onset of dementia, but many of them are caused by damage and degeneration of neurons. Neurons, which extend long neurites, are specialized to convey stimulus information. Therefore, conventionally, pharmaceuticals have been developed which inhibit damage and degeneration of neurons.

The inventors of the present application have been developing pharmaceuticals and functional foods using *wasabi* components for many years, as can be seen in Japanese Unexamined Patent Application Publication Nos. 2010-202559 and 2015-051927. The inventors attempted to promote extension of neurons using *wasabi* components.

In addition, maintenance and improvement of brain function such as memory, learning skills and the like are required for a wide generation, from the young to the elderly, including students and social workers who study for examinations for entrance, certificate or the like.

Diseases caused by decrease in brain function include not only dementia represented by Alzheimer's disease but also mental disease such as depression and delirium. One cause of the decrease in brain function is death of neurons. Death of neurons is said to be caused by accumulation of amyloid $\beta$ and the like. When amyloid $\beta$ becomes fibrotic and accumulates as a lump (senile plaque) inside the brain, anomalous change of tau protein and synapse is caused by the influence. This anomalous change impairs substance transport inside neurons and information transmission between neurons, thereby decreasing brain function.

In recent years, natural materials are being searched that are effective for inhibition and improvement of deterioration of brain function. As such natural materials, for example, rosemary, rice bran and the like (Japanese Unexamined Patent Application Publication No. 2013-526865), ginkgo leaf, curcumin, astaxanthin and the like (Japanese Unexamined Patent Application Publication No. 2015-107960) are known. Also, DHA and the like are known to be effective in reducing amyloid $\beta$ (Japanese Unexamined Patent Application Publication No. 2015-147775).

At present, it is strongly desired to further find substances effective for inhibiting deterioration of brain function, improving brain function, and to investigate applicability to pharmaceuticals.

SUMMARY

It is preferable to provide a novel neuron activator in the present disclosure.

In one aspect of the present disclosure, it is desirable to provide a novel dopamine production promotor that can promote dopamine-producing ability of neurons.

In another aspect of the present disclosure, it is desirable to provide a neuron extension promotor that can promote extension of neurons.

In further another aspect of the present disclosure, it is desirable to provide an amyloid $\beta$ resistance enhancer that can enhance resistance of neurons against amyloid $\beta$.

A neuron activator of the present disclosure that activates neurons comprises at least one selected from the group consisting of a dopamine production promotor that promotes dopamine production of the neurons, a neuron extension promotor that promotes extension of the neurons, and an amyloid $\beta$ resistance enhancer that enhances resistance of the neurons against amyloid $\beta$. The neuron activator includes 6-methylsulfinylhexyl isothiocyanates or glycosides thereof, and at least one selected from the group consisting of unsaturated fatty acid and polyphenol.

BRIEF DESCRIPTION OF THE DRAWINGS

An example embodiment of the present disclosure will be described hereinafter with reference to the accompanying drawings, in which.

DETAILED DESCRIPTION OF THE PREFERRED EMBODIMENTS

Figure 1:
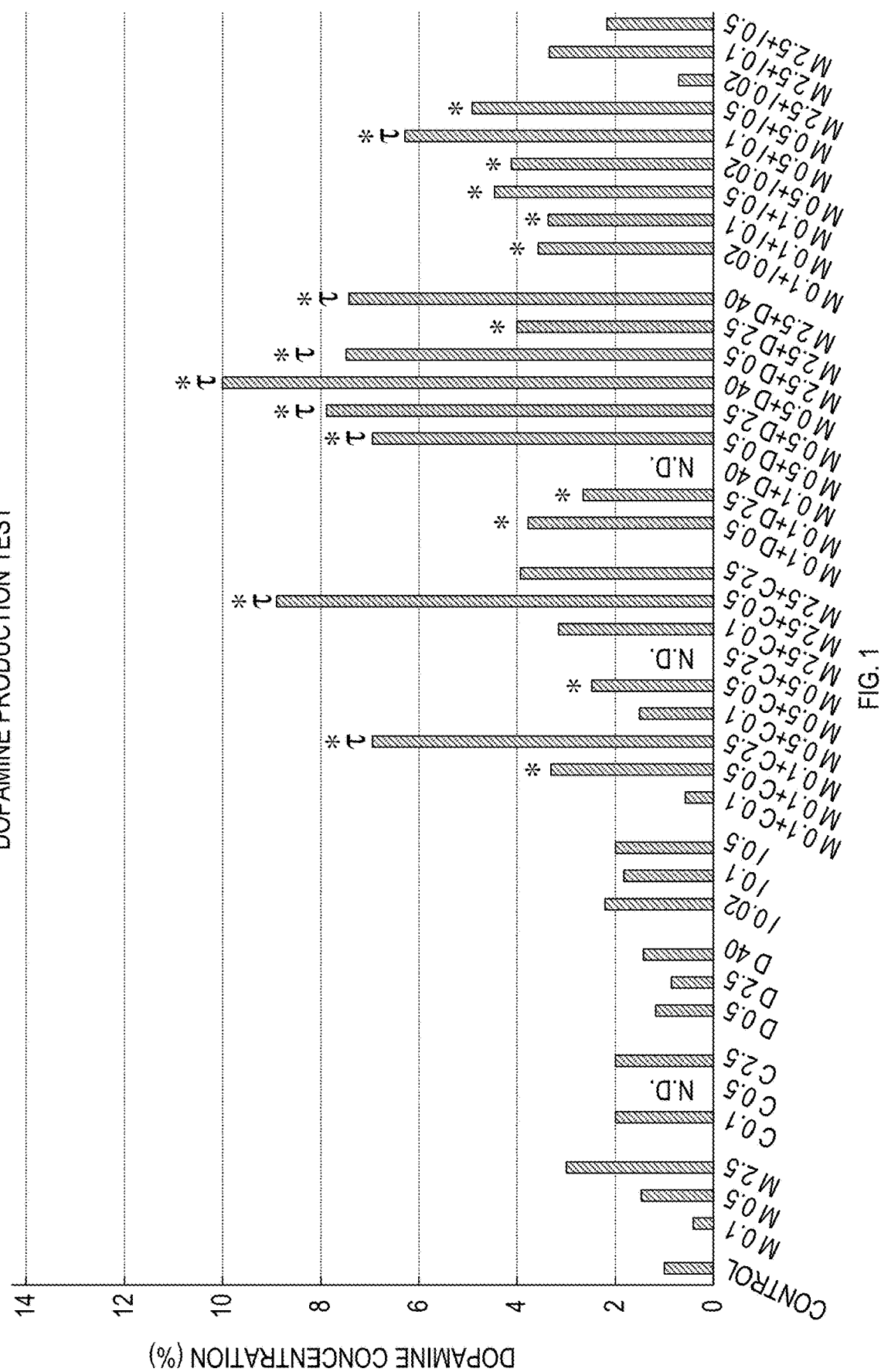
FIG. 1 is a diagram showing results of a dopamine production test according to Experimental example 1.

An embodiment of the present disclosure provides a neuron activator that activates neurons. The neuron activator comprises at least one selected from the group consisting of a dopamine production promotor that promotes dopamine production of neurons, a neuron extension promotor that promotes extension of the neurons, and an amyloid β resistance enhancer that enhances resistance of the neurons against amyloid β.

The neuron activator of the present embodiment includes (A) isothiocyanates such as 6-methylsulfinylhexyl isothiocyanates (hereinafter, also referred to as "6-MSITCs") or glycosides thereof, and at least one selected from the group consisting of (B) unsaturated fatty acid and (C) polyphenol.

In the present embodiment, the dopamine production promotor includes at least one selected from the group consisting of (A) isothiocyanates such as 6-methylsulfinylhexyl isothiocyanates or glycosides thereof, (B) unsaturated fatty acid and (C) polyphenol.

According to the dopamine production promotor of the present embodiment, dopamine-producing ability of the neurons can be promoted. The dopamine production promotor of the present embodiment promotes production of dopamine by the neurons.

In the present embodiment, the neuron extension promotor includes (A) isothiocyanates such as 6-methylsulfinylhexyl isothiocyanates or glycosides thereof, and at lease one selected from the group consisting of (B) unsaturated fatty acid, and (C) polyphenol.

According to the neuron extension promotor of the present embodiment, extension of the neurons can be promoted. The neuron extension promotor promotes neurite extension of the neurons.

In the present embodiment, the amyloid β resistance enhancer includes (A) isothiocyanates such as 6-methylsulfinylhexyl isothiocyanates or glycosides thereof, and at least one selected from the group consisting of (B) unsaturated fatty acid and (C) polyphenol.

According to the amyloid β resistance enhancer of the present embodiment, resistance of the neurons against amyloid β can be enhanced. The amyloid β resistance enhancer of the present embodiment can increase resistance of the neurons against amyloid β and protect the neurons.

(A) 6-MSITCs, and at least one selected from the group consisting of (B) unsaturated fatty acid and (C) polyphenol are constituents of the neuron activator, especially of the dopamine production promotor, the neuron extension promotor, and the amyloid β resistance enhancer. Hereinafter, description on (A) 6-MSITCs, (B) unsaturated fatty acid, and (C) polyphenol will be given.

(A) Isothiocyanates

In the present embodiment, isothiocyanates refer to a compound having a —NCS group. Isothiocyanates may, for example, have an aliphatic or an aromatic group as a side chain. Examples of isothiocyanates having an aliphatic group include at least one selected from the group consisting of isopropyl isothiocyanate, isobutyl isothiocyanate, 2-butyl isothiocyanate, isoamyl isothiocyanate, amyl isothiocyanate, allyl isothiocyanate, 3-butenyl isothiocyanate, 4-pentenyl Isothiocyanate, 5-hexenyl isothiocyanate, 6-heptenyl isothiocyanate, 3-methylthiopropyl isothiocyanate, 4-methylthiobutyl isothiocyanate, 5-methylthiopentyl isothiocyanate, 6-methylthiohexyl isothiocyanate, 7-methylthioheptyl isothiocyanate, 4-methylsulfinylbutyl isothiocyanate, 5-methylsulfinyl pentyl isothiocyanate, 6-methylsulfinyl-hexyl isothiocyanate, 6-methylsulfinylhexyl isothiocyanates (6-MSITCs), and 7-methylsulfinylheptyl isothiocyanate. Among them, 4-methylsulfinylbutyl isothiocyanate. 5-methylsulfinyl pentyl isothiocyanate, 6-MSITCs, and 7-methylsulfinylheptyl isothiocyanate are preferable. An example of isothiocyanates having an aromatic group includes phenethyl isothiocyanate.

In the present embodiment, isothiocyanates include glycosides.

In the present embodiment, preferred isothiocyanates are 6-MSITCs or glycosides thereof.

In the present embodiment, 6-MSITCs include 6-MSITC and 6-MSITC analogs. 6-MSITC is represented by a chemical formula below.

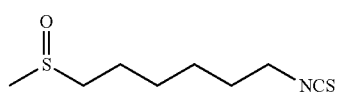

[Formula 1]

In the present embodiment, 6-MSITC analogs include naturally occurring analogs of 6-MSITC, and synthetically obtained, non-naturally occurring analogs of 6-MSITC. Examples of 6-MSITC analogs include 6-MSITC (having a structure of non-oxidized sulfur, that is, a structure containing a methyl sulfide group) and 6-MSITC (having a structure of peroxidized sulfur, that is, a structure containing a methylsulfonyl group), and the like.

6-MSITCs used in the present embodiment are contained in Brassicaceae plants, for example. Among Brassicaceae, hon-*wasabi* and/or horseradish contain many 6-MSITCs.

6-MSITCs used in the present embodiment can be obtained by chemical synthesis, but may be extracted from plants and purified. Examples of plants that can be raw materials for 6-MSITCs include Bataceae, Brassicaceae, Bretschneideraceae, Capparaceae, Caricaceae, Euphorbiaceae, Gyrostemonaceae, Limnanthaceae, Moringacea, Pentadiplandraceae, Phytolaccaceae, Pittosporaceae, Resedaceae, Salvadoraceae, Tovariaceae, Tropaeolaceae and the like. More specifically, the examples include *wasabi* (*Wasabia japonica*) [also known as hon-*wasabi*], horseradish (*Armoracia rusticana*) [also known as *Yama-wasabi*], *Batis maritima*, mustard (*Brassica juncea*), broccoli (*Brassica oleracea* var. *italica*), mouse-ear cress (*Arabidopsis thaliana*), shepherd's purse (*Capsella bursa-pastoris*), watercress (*Nasturtium officinale*), *Bretschneidera sinensis*, caper (*Capparis spinosa*), papaya (*Carica papaya*), *Drypetes roxburghii*, *Putranjiva roxburghii*, *Tersonia brevipes*, *Limnanthes douglasii*, horseradish tree (*Moringa oleifera*), *Pentadiplandra brazzeana*, pokeweed (*Phytolacca americana*), *Bursaris spinose* var. *incana*, white mignonette (*Reseda alba*), *Salvadora persica*, *Tovaria pendula*, Indian cress (*Tropaeolum majus*) and the like. 6-MSITCs that can be used in the present disclosure are not limited to those obtained from the above plants. All natural resources that contain 6-MSITCs can be used as raw materials.

Examples of extracting and purifying methods from the above plants include a method of extracting 6-MSITCs from *wasabi* and horseradish which are Brassicaceae plants. A preferred purifying method is disclosed in Japanese Patent No. 3919489.

In the present embodiment, glycosides of 6-MSITCs are compounds in which sugar residues are bonded to 6-MSITCs. Preferred sugar residues which are bonded to 6-MSITCs include at least one sugar selected from the group consisting of glucose, rhamnose, fructose, and galactose. Glucose is more preferred. The sugar residue may be either monosaccharide or polysaccharide, and monosaccharide is preferred. Monosaccharide refers to sugar consisting of a monosaccharide molecule. Polysaccharide refers to a sugar chain in which two or more monosaccharide molecules are bonded. It is preferable that the polysaccharide is formed by bonding two to ten monosaccharides. It is further preferable that the polysaccharide is formed by bonding two to five monosaccharides.

It is preferable that the sugar residues are bonded to 6-MSITCs at a positon of the —NCS group, more preferably bonded to S.

Examples of glycoside of 6-MSITCs include glucohesperin. Glucohesperin is a compound represented by a chemical formula below.

[Formula 2]

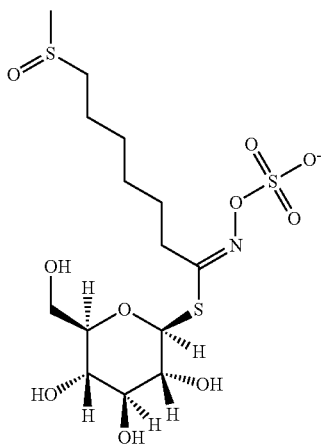

Glycosides of 6-MSITCs can be obtained from plants containing glycosides of 6-MSITCs, such as hon-*wasabi*. For example, enzyme reaction of the plants is stopped by a method such as heating (by electromagnetic wave, far infrared ray, calcination, or the like), drying, freezing, enzyme treatment, chemical treatment, and the like. Thereafter, solvent extraction or squeezing by water, organic solvent or the like, drying, pulverization, purification, enzyme reaction, chemical reaction and the like are carried out. Thereby, glycosides of 6-MSITCs are extracted or separated, and purified. In addition, glycosides of 6-MSITCs can be obtained by chemical synthesis.

(B) Unsaturated Fatty Acid

Unsaturated fatty acid refers to a fatty acid having at least one double bond. Preferred unsaturated fatty acid has two or more double bonds. The number of carbons of unsaturated fatty acid is not particularly limited, but preferably 12 to 24, more preferably 15 to 24, and further preferably 18 to 22.

It is preferable that unsaturated fatty acid has double bonds at least in one of ω-3 position, ω-6 position, and ω-9 position. Specifically, it is preferable that unsaturated fatty acid is ω-3 fatty acid.

Ω-3 fatty acid has a double bond at least in the ω-3 position of the fatty acid. Examples of the unsaturated fatty acid having a double bond in the ω-3 position include docosahexaenoic acid (DHA, $22:6(\Delta^{4,\ 7,\ 10,\ 13,\ 16,\ 19})$), docosapentaenoic acid (DPA, $22:5(\Delta^{7,\ 10,\ 13,\ 16,\ 19})$), eicosapentaenoic acid (EPA, $20:5(\Delta^{5,\ 8,\ 11,\ 14,\ 17})$), and α-linolenic acid (ALA, $18:3(\Delta^{9,\ 12,\ 15})$).

It is preferable that the ω-3 fatty acid is extracted from fish and shellfish and/or fish oil. DHA is included in, for example, blue fish. EPA is included in fish oil of such as cod, herring, mackerel, salmon, sardine, and krill. Among these, DHA and EPA are preferred. DHA is more preferable.

(C) Polyphenol

In the present embodiment, polyphenol is a generic term for compounds having a plurality of phenolic hydroxy groups in a molecule. Polyphenol preferably includes at least one selected from the group consisting of curcuminoid and flavonoid.

Curcuminoid may be represented by a formula (I) below.

[Formula 3]

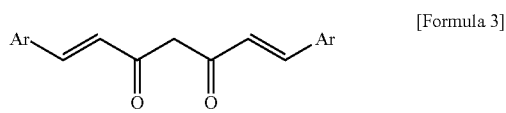

(In the formula, Ar represents an aromatic group having an OH group.)

Examples of curcuminoid include curcumin dimethoxy curcumin and bis dimethoxy curcumin. Among these, curcumin is preferred. Examples of curcumin are represented by formulas (I-I) to (I-IV) below.

[Formula 4]

(I-I)

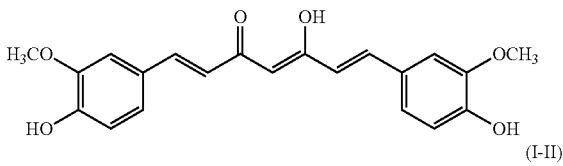

(I-II)

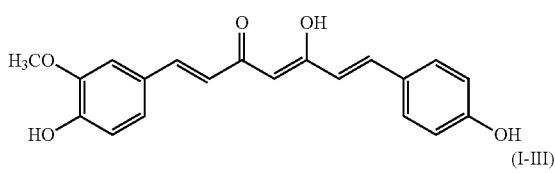

(I-III)

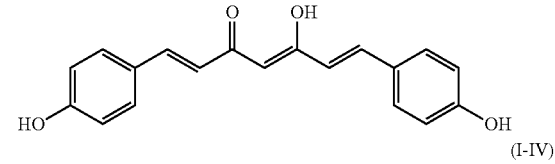

(I-IV)

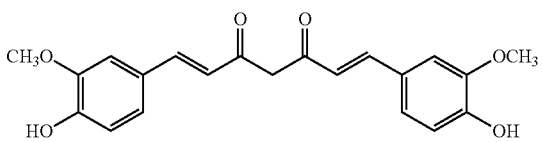

Examples of components having curcumins include turmeric extract, turmeric pigment, or the like.

It is preferable that curcuminoid is extracted from turmeric. Curcuminoid including curcumins can be obtained, for example, by extraction separation from turmeric or the like as a raw material, using organic solvent such as alcohol solvent, or by synthesis.

It is preferable that flavonoid is a flavonol represented by a formula (II) below.

[Formula 5]

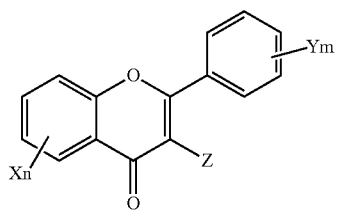

(II)

(In the formula, X represents —O⁻ or —OH, Y represents —O⁻ or —OH, Z represents —O⁻ or —OH, and X, Y and Z together have two or more —OH. Also, n represents an integer of 1 to 4, and m represents an integer of 1 to 5.)

Examples of flavonol include those represented by formulas (II-I) to (II-XI) below. Among these, isorhamnetin represented by the formula (II-III) is preferred.

[Formula 6]

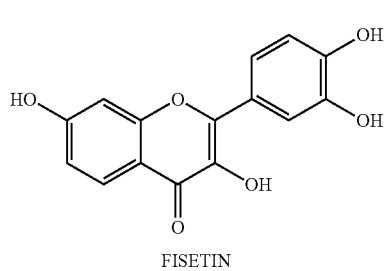

FISETIN (II-I)

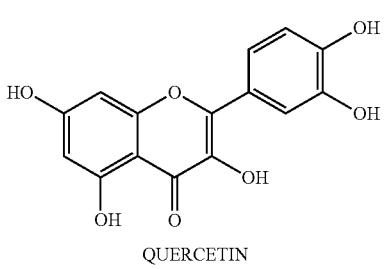

QUERCETIN (II-II)

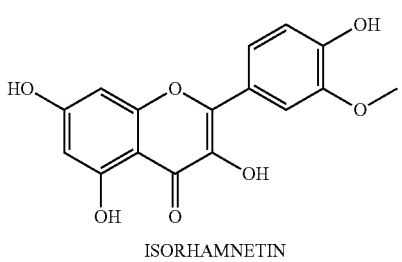

ISORHAMNETIN (II-III)

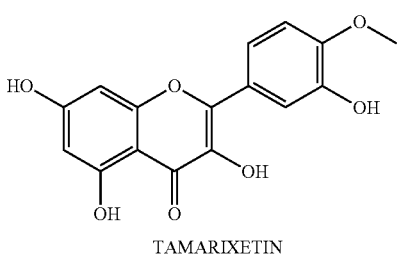

TAMARIXETIN (II-IV)

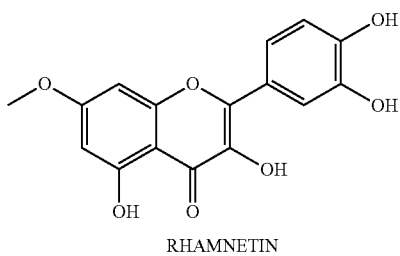

RHAMNETIN (II-V)

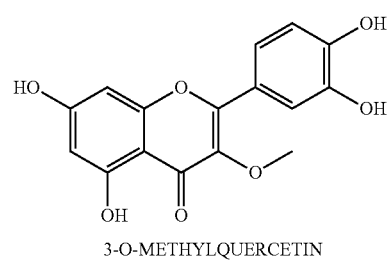

3-O-METHYLQUERCETIN (II-VI)

[Formula 7]

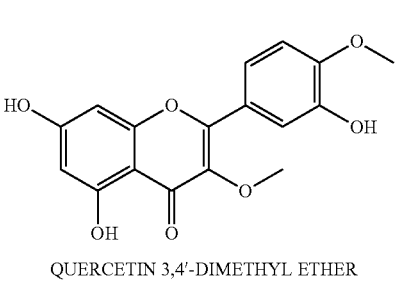

QUERCETIN 3,4'-DIMETHYL ETHER (II-VII)

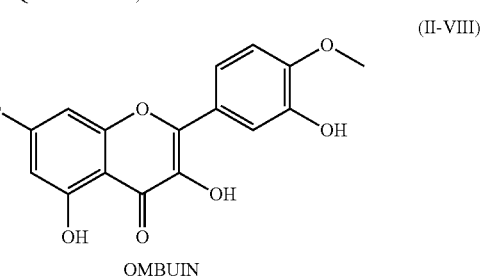

OMBUIN (II-VIII)

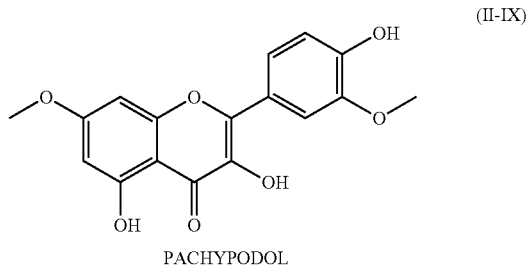

PACHYPODOL (II-IX)

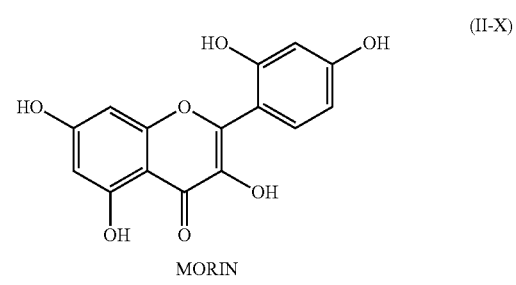

MORIN (II-X)

-continued

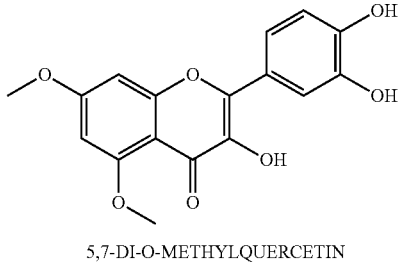

(II-XI)

5,7-DI-O-METHYLQUERCETIN

An example of components including isorhamnetin is gingko extract.

It is preferable that flavonoid is extracted from ginkgo leaves. Flavonoid can be obtained by a known extraction method from flavonoid-containing plants, or a known synthesis method. Isorhamnetin can be extracted from ginkgo leaves by a known method.

It is preferable that the neuron activator of the present embodiment may include each of 6-MSITCs, docosahexaenoic acid (DHA), curcumin, and isorhamnetin alone or in combination of two or more.

The neuron activator of the present embodiment may have a combination of the following components:
6-MSITCs and DHA,
6-MSITCs and curcumin, or
6-MSITCs and isorhamnetin.

The neuron activator of the present embodiment may further contain an additive. As the additive, for example, an excipient, a disintegrant, a binder, an antioxidant, a coating agent, a coloring agent, a corrigent, a surfactant, a plasticizer and the like can be blended.

Also, in the neuron activator of the present embodiment, antiallergic agents, cooling agents, vitamines, and other crude drugs can be blended as long as the effect of the neuron activator is not impaired.

The neuron activator of the present embodiment may be contained in foods, quasi-drugs, and pharmaceuticals.

The form of foods containing the neuron activator of the present embodiment is not limited. Specific examples of food forms include general foods, general drinks, supplements, health foods, special purpose foods, foods with health claims such as foods with function claims and foods for specified health, soft drinks, tea drinks, health drinks, alcoholic beverages such as wines, confectioneries, cooked rices, breads, noodles, side dishes, seasonings, and the like.

The usage of quasi-drugs and pharmaceuticals containing the neuron activator of the present embodiment is not limited. For example, the quasi-drugs and the pharmaceuticals may be used as internal/external preparations.

The dosage form of quasi-drugs and pharmaceuticals containing the neuron activator of the present embodiment is not limited. Example dosage forms include capsules, tablets, powders, granules, solutions, and the like.

The neuron activator of the present embodiment includes at least one selected from the group consisting of a dopamine production promotor, a neuron extension promotor, and an amyloid β resistance enhancer, and can be used for inhibiting or treating diseases or symptoms involving neurons.

The neuron activator of the present embodiment can be used for inhibition or treatment of neurological disorders selected from the group consisting of, for example, dementia, type 2 diabetes, Alzheimer-type dementia, diabetes, Parkinson's disease, transmissible spongiform encephalopathy commonly known as "mad cow disease", medullary thyroid carcinoma, arrhythmia, arteriosclerosis, rheumatoid arthritis, aortic medial amyloid, prolactinomas, familial amyloid polyneuropathy, hereditary non-neuropathic amyloidosis, dialysis amyloidosis, Finnish amyloidosis, lattice corneal dystrophy, cerebral amyloid angiopathy, systemic AL amyloidosis, sporadic inclusion body myositis, pheochromocytoma, osteomyelitis, multiple myeloma, encephalitis, meningitis, pre-Alzheimer's disease, mild cognitive impairment, early-onset Alzheimer's disease, late-stage Alzheimer's disease, age-related dementia, Huntington's disease, multiple sclerosis, amyotrophic lateral sclerosis (ALS or Lou Gehrig's disease), prion disease, Creutzfeldt-Jakob disease, Lewy body disease, Friedreich's ataxia, stroke, genetic brain injury, schizophrenia, depression, bipolar disorder, attention deficit hyperactivity disorder (ADHD), autism, Asperger's syndrome, and Down's syndrome.

The neuron activator of the present embodiment is suitable for the following uses:
pharmaceutical composition for activating neuron including the neuron activator,
food composition for activating neuron including the neuron activator,
application for producing a neuron activator,
application for producing pharmaceutical compositions for activating neurons including the neuron activator;
application for producing food compositions for activating neurons including the neuron activator;
method for improving neurons including administering the neuron activator to a subject;
a method for improving neurons including administering the pharmaceutical composition for activating neurons to a subject,
a method for improving neurons including administering the food composition for activating neurons to a subject, and
use of a composition for producing a neuron activator that activates neurons, the neuron activator comprising at least one selected from the group consisting of: a dopamine production promotor that promotes dopamine production of the neurons, a neuron extension promotor that promotes extension of the neurons, and an amyloid β resistance enhancer that enhances resistance of the neurons against amyloid β, the composition including 6-methylsulfinylhexyl isothiocyanates or glycosides thereof, and at least one selected from the group consisting of unsaturated fatty acid and polyphenol.

[Dopamine Production Promotor]

The neuron activator of the present embodiment may be a dopamine production promotor. When the dopamine production promotor of the present embodiment includes (A) 6-MSITCs and (B) docosahexaenoic acid (DHA), it is preferable that a molar ratio of (B) DHA to (A) 6-MSITCs is 0.2 to 400, more preferably 0.2 to 80, and further preferably 1 to 80.

When the dopamine production promotor of the present embodiment includes (A) 6-MSITCs and (CI) curcumin, it is preferable that a molar ratio of (CI) curcumin to (A) 6-MSITCs is 0.04 to 25, more preferably 0.2 to 25.

When the dopamine production promotor of the present embodiment includes (A) 6-MSITCs and (CII) isorhamnetin, it is preferable that a molar ratio of (CII) isorhamnetin to (A) 6-MSITCs is 0.008 to 5, more preferably 0.04 to 0.2.

In these cases, it is possible to more effectively promote the effect of producing dopamine from neurons.

The dosage of the dopamine production promotor of the present embodiment is determined in consideration of a patient's age, sex, body weight, usage, dose, and the like. Usage includes oral administration, vascular injection, external application, and the like. In case of oral administration, it is preferable that daily dosage of 6-MSITCs in the dopamine production promotor is 10 µg to 100 mg/day, the dosage of unsaturated fatty acid is 100 mg to 10 g/day, and the dosage of polyphenol is 0.1 mg to 10 g/day.

When the usage of the dopamine production promotor of the present embodiment is vascular injection, it is preferable that the daily dosage of 6-MSITCs in the dopamine production promotor is 1 µg to 5 mg/day, the dosage of unsaturated fatty acid is 1 mg to 100 mg/day, and the dosage of polyphenol is 0.1 µg to 1 mg/day.

The dopamine production promotor of the present embodiment is suitable for the following uses:
  pharmaceutical composition for promoting dopamine production including the dopamine production promotor,
  food composition for promoting dopamine production including the dopamine production promotor,
  application for producing the dopamine production promotor,
  application for producing pharmaceutical compositions for promoting dopamine production including the dopamine production promotor,
  application for producing food compositions for promoting dopamine production including the dopamine production promotor,
  a method for promoting dopamine production including administering the dopamine production promotor to a subject,
  a method for promoting dopamine production including administering the pharmaceutical composition for promoting dopamine production to a subject, and
  a method for promoting dopamine production including administering the food composition for promoting dopamine production to a subject.

[Neuron Extension Promotor]

The neuron activator of the present embodiment may be a neuron extension promotor.

When the neuron extension promotor of the present embodiment includes (A) 6-MSITCs and (B) docosahexaenoic acid (DHA), it is preferable that a molar ratio of (B) DHA to (A) 6-MSITCs is 0.2 to 400, more preferably 0.2 to 80, and further preferably 0.2 to 16.

When the neuron extension promotor of the present embodiment includes (A) 6-MSITCs and (CI) curcumin, it is preferable that a molar ratio of (CI) curcumin to (A) 6-MSITCs is 0.04 to 25, more preferably 0.04 to 1, further preferably 0.2 to 1.

When the neuron extension promotor of the present embodiment includes (A) 6-MSITCs and (CII) isorhamnetin, it is preferable that a molar ratio of (CII) isorhamnetin to (A) 6-MSITCs is 0.008 to 5, more preferably 0.008 to 1.0, further preferably 0.008 to 0.2.

In these cases, it is possible to more effectively promote the effect of extending neurites.

The dosage of the neuron extension promotor of the present embodiment is determined in consideration of a patient's age, sex, body weight, usage, dose, and the like. Usage includes oral administration, vascular injection, external application, and the like. In case of oral administration, it is preferable that daily dosage of 6-MSITCs in the neuron extension promotor is 10 µg to 100 mg/day, the dosage of unsaturated fatty acid is 100 mg to 10 g/day, and the dosage of polyphenol is 0.1 mg to 10 g/day.

When the usage of the neuron extension promotor of the present embodiment is vascular injection, it is preferable that the daily dosage of 6-MSITCs in the neuron extension promotor is 1 µg to 5 mg/day, the dosage of unsaturated fatty acid is 1 mg to 100 mg/day, and the dosage of polyphenol is 0.1 µg to 1 mg/day.

The neuron extension promotor of the present embodiment is suitable for the following uses:
  pharmaceutical composition for promoting neuron extension including the neuron extension promotor,
  food composition for promoting neuron extension including the neuron extension promotor,
  application for producing the neuron extension promotor,
  application for producing pharmaceutical compositions for promoting neuron extension including the neuron extension promotor,
  application for producing food compositions for promoting neuron extension including the neuron extension promotor,
  a method for promoting neuron extension including administering the neuron extension promotor to a subject,
  a method for promoting neuron extension including administering the pharmaceutical composition for promoting neuron extension to a subject, and
  a method for promoting neuron extension including administering the food composition for promoting neuron extension to a subject.

[Amyloid β Resistance Enhancer]

The neuron activator of the present embodiment may be an amyloid β resistance enhancer.

The amyloid β resistance enhancer of the present embodiment includes 6-methylsulfinylhexyl isothiocyanates or glycosides thereof.

When the amyloid β resistance enhancer of the present embodiment includes (A) 6-MSITCs and (B) docosahexaenoic acid (DHA), it is preferable that a molar ratio of (B) DHA to (A) 6-MSITCs is 0.2 to 400, more preferably 0.2 to 80, and further preferably 1 to 80.

When the amyloid β resistance enhancer of the present embodiment includes (A) 6-MSITCs and (CI) curcumin, it is preferable that a molar ratio of (CI) curcumin to (A) 6-MSITCs is 0.04 to 25, more preferably 0.2 to 25.

When the amyloid β resistance enhancer of the present embodiment includes (A) 6-MSITCs and (CII) isorhamnetin, it is preferable that a molar ratio of (CII) isorhamnetin to (A) 6-MSITCs is 0.008 to 5, more preferably 0.04 to 0.2.

In these cases, it is possible to more effectively increase resistance of neurons against amyloid β.

The dosage of the amyloid β resistance enhancer of the present embodiment is determined in consideration of a patient's age, sex, body weight, usage, dose, and the like. Usage includes oral administration, vascular injection, external application, and the like. In case of oral administration, it is preferable that daily dosage of 6-MSITCs in the amyloid β resistance enhancer is 10 µg to 100 mg/day, the dosage of unsaturated fatty acid is 100 mg to 10 g/day, and the dosage of polyphenol is 0.1 mg to 10 g/day.

When the usage of the amyloid β resistance enhancer of the present embodiment is vascular injection, it is preferable that the daily dosage of 6-MSITCs in the amyloid β resistance enhancer is 1 µg to 5 mg/day, the dosage of unsaturated fatty acid is 1 mg to 100 mg/day, and the dosage of polyphenol is 0.1 µg to 1 mg/day.

The amyloid β resistance enhancer of the present embodiment is suitable for the following uses:

pharmaceutical composition for enhancing resistance against amyloid β including the amyloid β resistance enhancer, food composition for enhancing resistance against amyloid β including the amyloid β resistance enhancer, application for producing the amyloid β resistance enhancer, application for producing pharmaceutical compositions for enhancing resistance against amyloid β including the amyloid β resistance enhancer, application for producing food compositions for enhancing resistance against amyloid β including the amyloid β resistance enhancer, a method for enhancing resistance against amyloid β including administering the amyloid β resistance enhancer to a subject, a method for enhancing resistance against amyloid β including administering the pharmaceutical composition for enhancing resistance against amyloid β to a subject, and a method for enhancing resistance against amyloid β including administering the food composition for enhancing resistance against amyloid β to a subject.

EXAMPLES

Experimental Example 1

Dopamine production tests of PC12 cells, using various components, were carried out as follows.

(1) Preparation of Various Components (a) 6-MSITC (Component 1)

6-MSITC used in the present embodiment was chemically synthesized by Kinjirushi Co., Ltd. Particulars of a chemical synthesis method of 6-MSITC are described as follows.

The method by Kjaer et. al. was followed in principle. (Kjaer et. al., Acta Chem. Scand., 11, 1298, 1957). 6-chlorohexanol was refluxed with $CH_3$—SNa to obtain 6-methylthiohexanol. 6-methylthiohexanol was reacted with thionyl chloride ($SOCl_2$) to obtain 6-chlorohexyl methyl sulfide. Then, an amino group was introduced to 6-chlorohexyl methyl sulfide by phthalimide potassium salt using the Gabriel method to generate N-(6-methylthiohexyl)-phthalimide. Hydrazine hydrate was added and refluxed with N-(6-methylthiohexyl)-phthalimide so as to obtain 6-methylthiohexylamine. Then, thiocarbonyl chloride was reacted with 6-methylthiohexylamine to obtain 6-methylthiohexyl isothiocyanate.

Further, a methylthio group in the obtained 6-methylthiohexyl isothiocyanate was oxidized with m-chloroperbenzoic acid to obtain 6-methylsulfinylhexyl isothiocyanate (6-MSITC) (Morimitsu et. al., J. Biol. Chem., 277, 3456, 2002).

6-MSITC involved in the present disclosure is included in Brassicaceae plants and the like, and can be obtained by solvent extraction or pulverization from these plants.

100 mg of 6-MSITC was dissolved in DMSO (dimethylsulfoxide) solvent to prepare a 6-MSITC solution containing 100 mM of 6-MSITC.

(b) DHA (Component 2)

DHA (manufactured by Nacalai Tesque, Inc., Product No. 14122-64) was obtained. DHA was extracted from blue fish. 100 mg of DHA was dissolved in DMSO solvent to prepare a DHA solution containing 100 mM of DHA.

(c) Curcumin (Component 3)

Curcumin (CAS No. 458-37-7, manufactured by Tokyo Chemical Industry Co., Ltd., Product No. C2302) was obtained. Curcumin is represented by a chemical formula below.

[Formula 8]

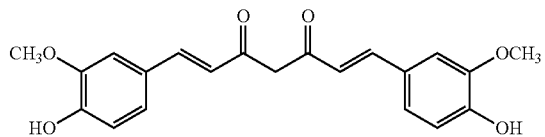

(I-IV)

This curcumin was synthesized. 67.56 mg of curcumin was dissolved in DMSO solvent to prepare a curcumin solution containing 200 mM of curcumin.

(d) Isorhamnetin (Component 4)

Isorhamnetin (manufactured by EXTRASYNTHESE, Product No. 11205) was obtained. Isorhamnetin was extracted from ginkgo leaves. 10 mg of isorhamnetin was dissolved in DMSO solvent using a pipette to prepare an isorhamnetin solution containing 10 mM of isorhamnetin.

(2) Preparation of Media

A growth medium A and a differentiation medium B containing the following components were prepared.

(a) Components in Growth Medium A

DMEM (Dulbecco's Modified Eagle Medium, manufactured by Nacalai Tesque, Inc., Product No. 08458-45)

10 wt % of horse serum (manufactured by Thermo Fisher Scientific Inc., Product No. 16050-122)

5 wt % of bovine serum (manufactured by Thermo Fisher Scientific Inc., Product No. 10437-028)

1 wt % of penicillin streptomycin (manufactured by Nacalai Tesque, Inc., Product No. 26253-84)

(b) Components in Differentiation Medium B

DMEM (Dulbecco's Modified Eagle Medium, manufactured by Nacalai Tesque, Inc., Product No. 08458-45)

2 wt % of horse serum (manufactured by Thermo Fisher Scientific Inc., Product No. 16050-122)

1 wt % of penicillin streptomycin (manufactured by Nacalai Tesque, Inc., Product No. 26253-84)

(3) PC12 Cell Proliferation

The above growth medium A was added to a flask for cell culture (manufacture by Thai Polypropylene Co., Ltd. (TPP)), and PC12 cells (manufactured by RIKEN, Product No. RCB0009) were further added for growth. PC12 cells are pheochromocytomas derived from rat's adrenal medulla, and are models of neuronal differentiation. When PC12 cells reached confluence of 80-90%, the grown PC12 cells were seeded in a new flask containing the growth medium A and subcultured. A ratio of the culture medium with the grown cells to the new growth medium A was 1:5 (volume ratio). Such passage was repeated at least three times.

(4) PC12 Cell Differentiation

In each well of a 96-well plate, 100 μl of growth medium A containing the post-passage PC12 cells obtained in the above step (3) at a concentration of $5 \times 10^4$/ml was seeded. The plate was left overnight at room temperature so as to stabilize the PC12 cells. The plate was centrifuged and the PC12 cells were allowed to settle in each well of the plate. Supernatants were removed. To each well in which the PC12 cells were settled, 100 μl of differentiation medium B was added and stirred, so as to suspend the PC12 cells in the differentiation medium B.

To the differentiation medium B in each well, NGF (manufactured by Sigma-Aldrich, Product No. N2513) was added. A concentration of NGF contained in the medium in all wells was 50 ng/ml.

Further, each of the components 1 to 4 prepared in the above step (1) was added to the medium in each well so as to achieve various concentrations in one kind or in combination of two kinds. Each sample is numbered 1 to 39. Table 1 shows concentrations of the components contained in each sample in the medium in each well.

TABLE 1

(Unit: µM)

| Sample | 6-MSITC | curcumin | DHA | isorhamnetin |
|---|---|---|---|---|
| C | | | | |
| 1 | 0.1 | | | |
| 2 | 0.5 | | | |
| 3 | 2.5 | | | |
| 4 | | 0.1 | | |
| 5 | | 0.5 | | |
| 6 | | 2.5 | | |
| 7 | | | 0.5 | |
| 8 | | | 2.5 | |
| 9 | | | 40 | |
| 10 | | | | 0.02 |
| 11 | | | | 0.1 |
| 12 | | | | 0.5 |
| 13 | 0.1 | 0.1 | | |
| 14 | 0.1 | 0.5 | | |
| 15 | 0.1 | 2.5 | | |
| 16 | 0.5 | 0.1 | | |
| 17 | 0.5 | 0.5 | | |
| 18 | 0.5 | 2.5 | | |
| 19 | 2.5 | 0.1 | | |
| 20 | 2.5 | 0.5 | | |
| 21 | 2.5 | 2.5 | | |
| 22 | 0.1 | | 0.5 | |
| 23 | 0.1 | | 2.5 | |
| 24 | 0.1 | | 40 | |
| 25 | 0.5 | | 0.5 | |
| 26 | 0.5 | | 2.5 | |
| 27 | 0.5 | | 40 | |
| 28 | 2.5 | | 0.5 | |
| 29 | 2.5 | | 2.5 | |
| 30 | 2.5 | | 40 | |
| 31 | 0.1 | | | 0.02 |
| 32 | 0.1 | | | 0.1 |
| 33 | 0.1 | | | 0.5 |
| 34 | 0.5 | | | 0.02 |
| 35 | 0.5 | | | 0.1 |
| 36 | 0.5 | | | 0.5 |
| 37 | 2.5 | | | 0.02 |
| 38 | 2.5 | | | 0.1 |
| 39 | 2.5 | | | 0.5 |

The plate was placed in a carbon dioxide incubator (5% $CO_2$, 37° C.), and the PC12 cells were cultured for 72 hours.

(5) Evaluation of Dopamine Production

A concentration of dopamine in each supernatant was measured. Measurement of dopamine concentration was carried out using ELIZA KIT (manufactured by ImmuSmol, Product No.: BA-E-5300) according to the specifications. A ratio of dopamine concentration in each supernatant was expressed as a percentage (%) of a control of which dopamine concentration in the supernatant is 1. Results of the measurement were shown in FIG. 1.

In FIG. 1, "M", "C", "D", and "I" sequentially mean "6-MSITC", "curcumin", "DHA", and "isorhamnetin". The same applies to FIGS. 2 to 5. In FIG. 1, τ means statistically significant. * means that synergistic effect was confirmed by combining two components. Synergistic effect herein means that use of two components in combination can produce more amount of dopamine than a sum of amounts of dopamine produced when each component is used alone.

Figure 2:
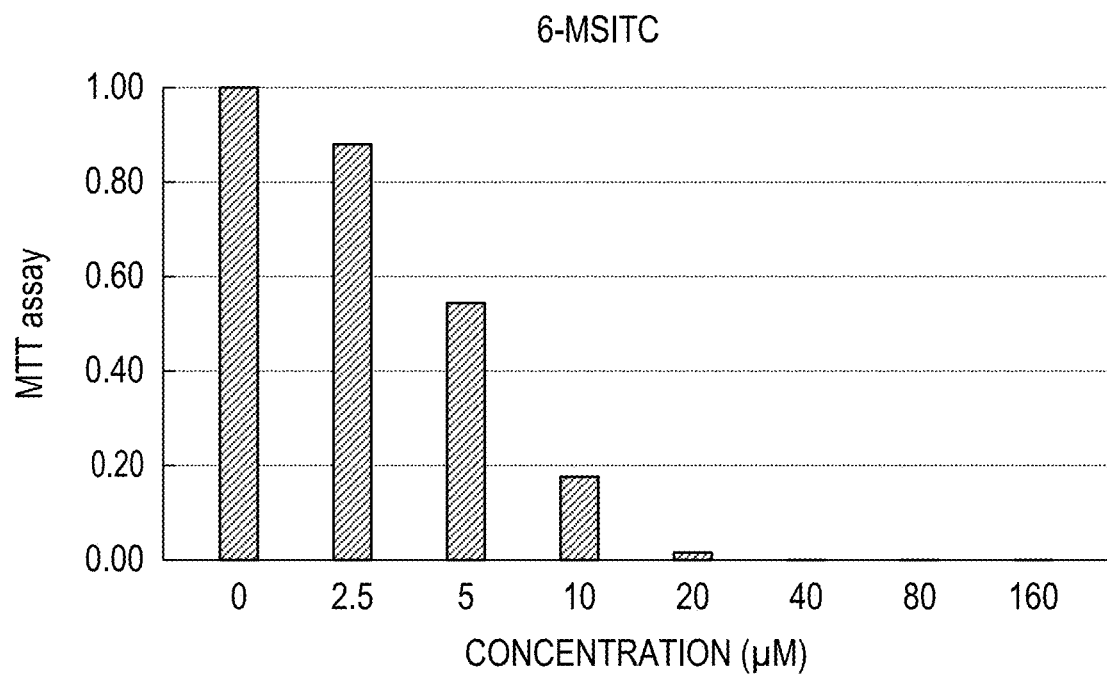
FIG. 2 is a diagram showing results of a toxicity test of 6-methylsulfinylhexyl isothiocyanate (6-MSITC) according to Experimental example 2.
Figure 3:
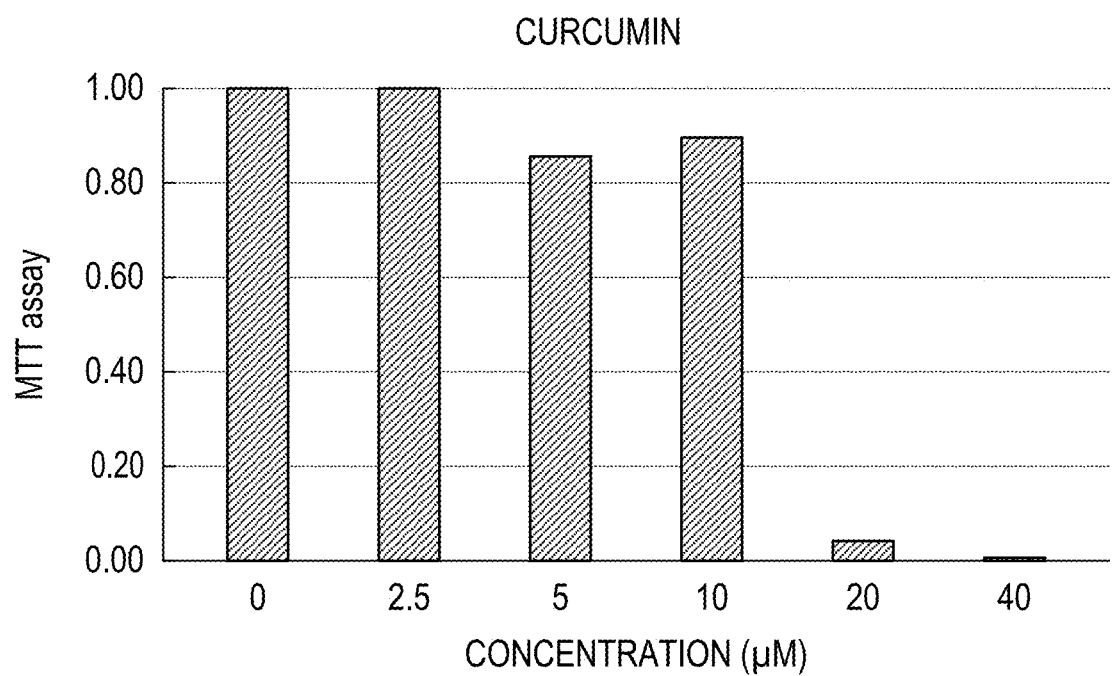
FIG. 3 is a diagram showing results of a toxicity test of curcumin to PC12 cells according to Experimental example 2.
Figure 4:
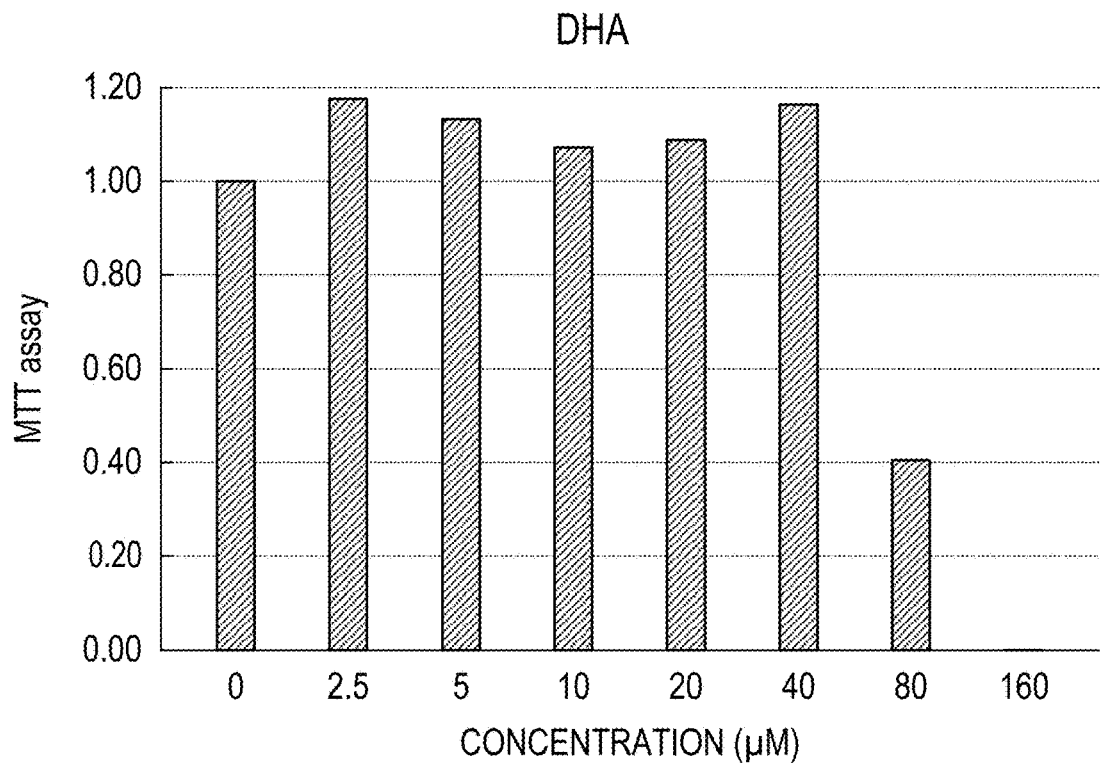
FIG. 4 is a diagram showing results of a toxicity test of DHA to PC12 cells according to Experimental example 2.
Figure 5:
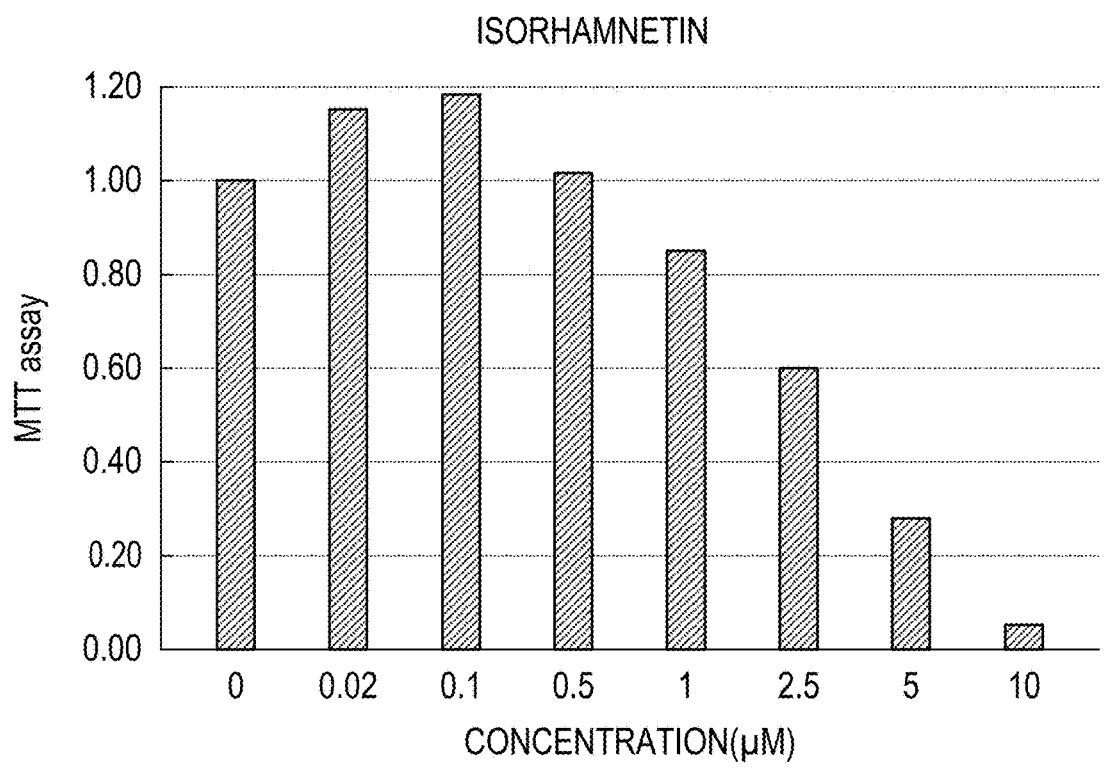
FIG. 5 is a diagram showing results of a toxicity test of isorhamnetin to PC12 cells according to Experimental example 2.

As shown in FIG. 2, dopamine-producing ability was enhanced by containing any one of 6-MSITC, curcumin, DHA, and isorhamnetin in the medium, as compared to a case without these components. Dopamine production effect of 6-MSITC was higher than those of curcumin, DHA, and isorhamnetin.

When 0.5 µM or 2.5 µM of 6-MSITC was added to the medium, the amount of dopamine production produced by the PC12 cells was higher than the control. When 0.1 µM or 2.5 µM of curcumin was added to the medium, the amount of dopamine production produced by the PC12 cells was higher than the control. When 0.5 µM or 40 µM of DHA was added to the medium, the amount of dopamine production produced by the PC12 cells was higher than the control. When 0.02 µM, 0.1 µM, or 0.5 µM of isorhamnetin was added to the medium, the amount of dopamine production produced by the PC12 cells was higher than the control.

There was a tendency that the amount of dopamine production was higher when 6-MSITC is combined with other components, as compared to a case in which one type of component was used. In combination of 6-MSITC and curcumin, the amount of dopamine production was higher when 6-MSITC is 0. 1 to 2.5 µM and curcumin is 0.1 to 2.5 µM. In combination of 6-MSITC and DHA, the amount of dopamine production was higher when 6-MSITC is 0.1 to 2.5 µM, and DHA is 0.5 to 40 µM. In combination of 6-MSITC and isorhamnetin, the amount of dopamine production was higher when 6-MSITC is 0.1 to 2.5 µM, and isorhamnetin is 0.02 to 0.5 µM.

Experimental Example 2

Toxicity of each component to PC12 cells was investigated using an MTT (3-(4,5-di-methylthiazol-2-yl)-2,5-diphenyltetrazolium bromide, yellow tetrazole) reagent.

In order to investigate toxicity of each component to PC12 cells, the PC12 cells were cultured in the same manner as in the above steps (1) to (4) of Experimental example 1, except for components added to the medium. The component added to the differentiation medium B in each well of (4) is any one of 6-MSITC (Component 1), curcumin (Component 3), DHA (Component 2), or isorhamnetin (Component 4). Concentrations of the respective components in the differentiation medium B were 0 (control), 2.5 µM, 5 µM, 10 µM, 20 µM, 40 µM, 80 µM, and 160 µM with respect to 6-MSITC (Component 1), 0 (control), 2.5 µM, 5 µM, 10 µM, 20 µM, and 40 µM with respect to curcumin (Component 3), 0 (control), 2.5 µM, 5 µM, 10 µM, 20 µM, 40 µM, 80 µM, and 160 µM with respect to DHA (Component 2), and 0 (control), 0.02 µM, 0 1 µM, 0.5 µM, 1 µM, 2.5 µM, 5 µM, and 10 µM with respect to isorhamnetin (Component 4).

After the PC12 cells were cultured for 72 hours in the above step (4) PC12 cell differentiation of Experimental example 1, 10 µl/well of MTT reagent (manufactured by Nacalai Tesque, Inc., Product No. 23547-21, MTT 5 mg/ml in a phosphate buffered saline) was added to the medium in each well. Further, the plate was placed in a carbon dioxide incubator (5% $CO_2$, 37° C.), and the PC12 cells were cultured for 4 hours.

The plate was centrifuged to allow the cells to settle in the wells. Supernatants were removed. To each well, 100 µl/well of DMSO was added, shaken and stirred to suspend the PC12 wells in DMSO to obtain a cell solution.

Absorbance of 490 nm was measured for the cell solution in each well. A fraction, of which denominator is absorbance of the cell solution of the control and numerator is absorbance of the cell solution of PC12 cells cultured in the culture medium including each sample, was converted into a decimal number, and a resulting value was shown as an MTT assay. Results of measurements in case of using 6-MSITC, curcumin, DHA, and isorhamnetin are sequentially shown in FIGS. 2, 3, 4, and 5.

In case of using 6-MSITC, curcumin, DHA, and isorhamnetin, the MTT assay was higher than the case of not using them (control). In view of the above, it was found that toxicity of 6-MSITC, curcumin, DHA, and isorhamnetin is low.

Experimental Example 3

Neurite extension tests of PC12 cells, using various components, were carried out as follows.

The above steps (1) Preparation of various components and (2) Preparation of media in Experimental example 1 were carried out to prepare 6-MSITC (Component 1), DHA (Component 2), curcumin (Component 3), the growth medium A, and differentiation medium B.

(3) PC12 Cell Proliferation

The above growth medium A was added to a flask for cell culture (manufactured by TPP), and PC12 cells (manufactured by RIKEN, Product No. RCB0009) were further added for growth. PC12 cells are pheochromocytomas derived from rat's adrenal medulla, and are models of neuronnal differentiation. When PC12 cells reached confluence of 80-90%, the grown PC12 cells were seeded in a new flask containing the growth medium A and subcultured. A ratio of the culture medium with the grown cells to the new growth medium A was 1:5 (volume ratio). Such passage was repeated at least three times.

(4) PC12 Cell Differentiation

In each well of a 96-well plate, 100 μl of growth medium A containing the post-passage PC12 cells obtained in the above step (3) at a concentration of $5 \times 10^4$/ml was seeded. The plate was left overnight at room temperature so as to stabilize the PC12 cells. The plate was centrifuged and the PC12 cells were allowed to settle in each well of the plate. Supernatants were removed. To each well in which the PC12 cells were settled, 100 μl of differentiation medium B was added and stirred, so as to suspend the PC12 cells in the differentiation medium B.

To the differentiation medium B in each well, NGF (manufactured by Sigma-Aldrich, Product No. N2513) was added. A concentration of NGF contained in the medium in all wells was 50 ng/ml.

Further, each of the components 1 to 4 prepared in the above step (1) of Experimental example 1 was added to the medium in each well so as to achieve various concentrations in one kind or in combination of two kinds. Each sample is numbered 1 to 39. Table 2 shows concentrations of the components contained in each sample in the medium in each well.

TABLE 2

(Unit: μM)

| Sample | 6-MSITC | curcumin | DHA | isorhamnetin |
|---|---|---|---|---|
| C | | | | |
| 1 | 0.1 | | | |
| 2 | 0.5 | | | |
| 3 | 2.5 | | | |
| 4 | | 0.1 | | |
| 5 | | 0.5 | | |
| 6 | | 2.5 | | |
| 7 | | | 0.5 | |
| 8 | | | 2.5 | |
| 9 | | | 40 | |
| 10 | | | | 0.02 |
| 11 | | | | 0.1 |
| 12 | | | | 0.5 |
| 13 | 0.1 | 0.1 | | |
| 14 | 0.1 | 0.5 | | |
| 15 | 0.1 | 2.5 | | |
| 16 | 0.5 | 0.1 | | |
| 17 | 0.5 | 0.5 | | |
| 18 | 0.5 | 2.5 | | |
| 19 | 2.5 | 0.1 | | |
| 20 | 2.5 | 0.5 | | |
| 21 | 2.5 | 2.5 | | |
| 22 | 0.1 | | 0.5 | |
| 23 | 0.1 | | 2.5 | |
| 24 | 0.1 | | 40 | |
| 25 | 0.5 | | 0.5 | |
| 26 | 0.5 | | 2.5 | |
| 27 | 0.5 | | 40 | |
| 28 | 2.5 | | 0.5 | |
| 29 | 2.5 | | 2.5 | |
| 30 | 2.5 | | 40 | |
| 31 | 0.1 | | | 0.02 |
| 32 | 0.1 | | | 0.1 |
| 33 | 0.1 | | | 0.5 |
| 34 | 0.5 | | | 0.02 |
| 35 | 0.5 | | | 0.1 |
| 36 | 0.5 | | | 0.5 |
| 37 | 2.5 | | | 0.02 |
| 38 | 2.5 | | | 0.1 |
| 39 | 2.5 | | | 0.5 |

The plate was placed in a carbon dioxide incubator (5% $CO_2$, 37° C.), and the PC12 cells were cultured for 72 hours.

(5) Evaluation of Cell Extension

Figure 6:
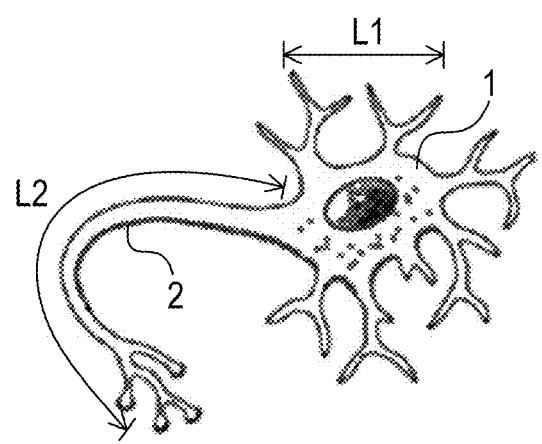
FIG. 6 is an explanatory view showing a neuron.
Figure 7:
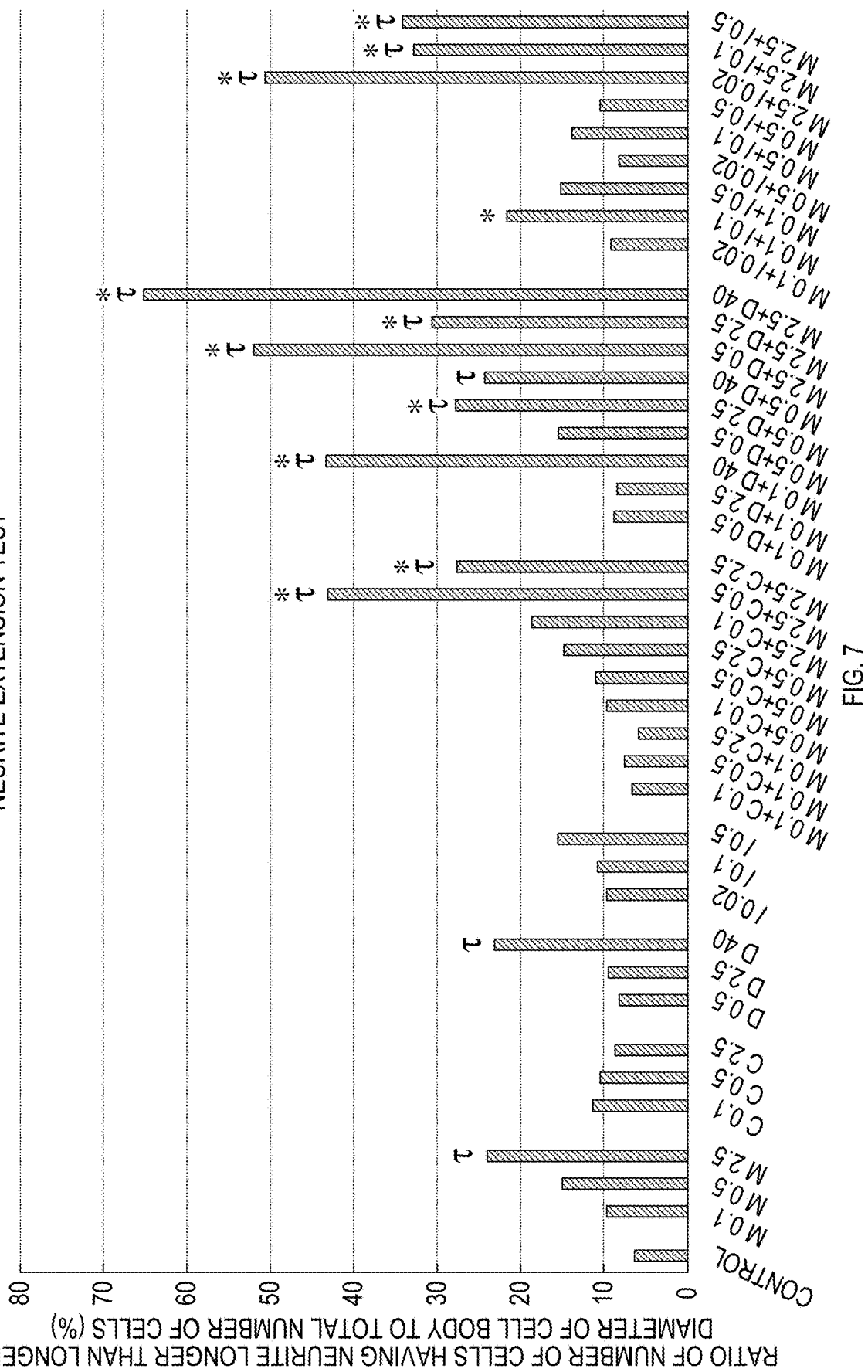
FIG. 7 is a diagram showing results of an extension test according to Experimental example 3.
Figure 8:
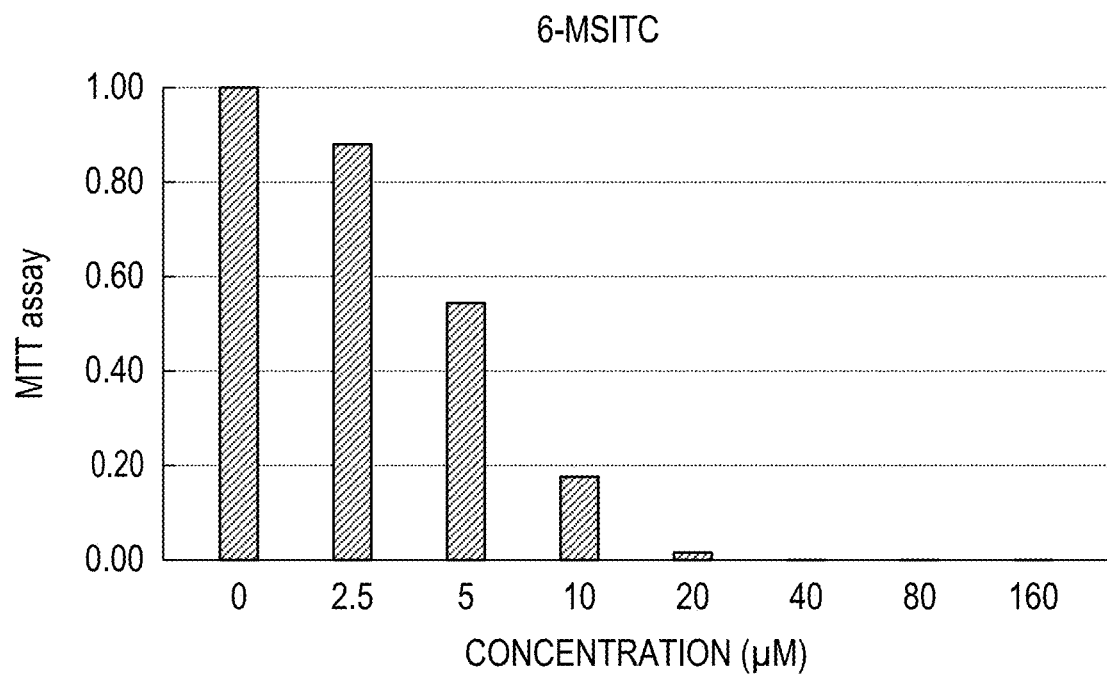
FIG. 8 is a diagram showing results of a toxicity test of 6-methylsulfinylhexyl isothiocyanate (6-MSITC) according to Experimental example 4.
Figure 9:
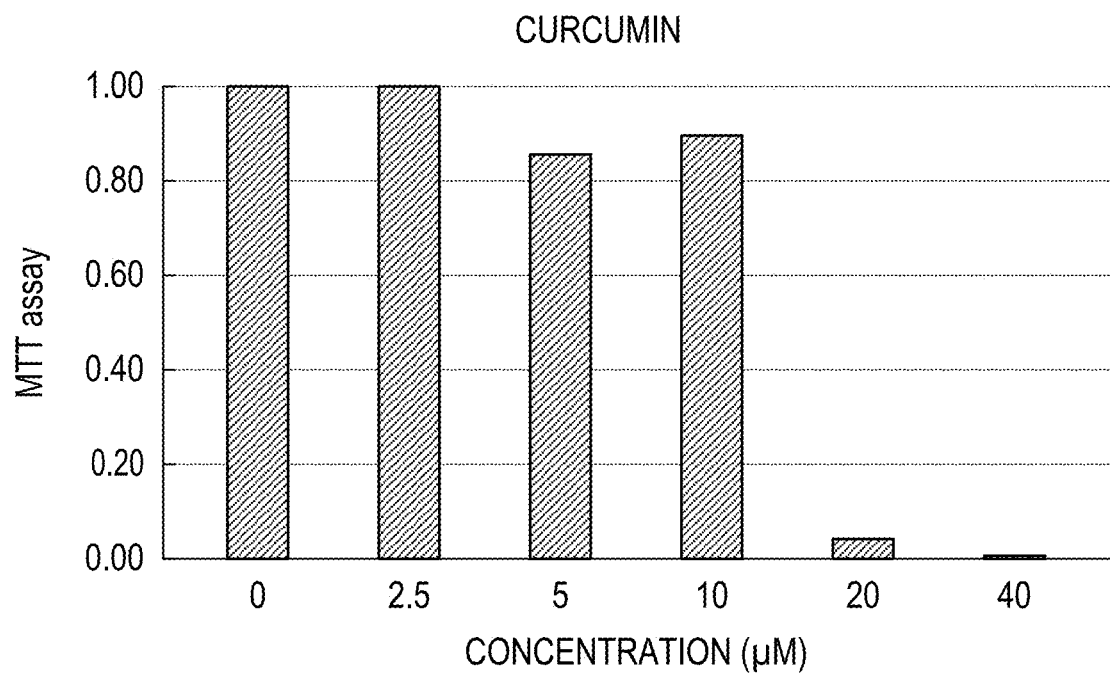
FIG. 9 is a diagram showing results of a toxicity test of curcumin according to Experimental example 4.
Figure 10:
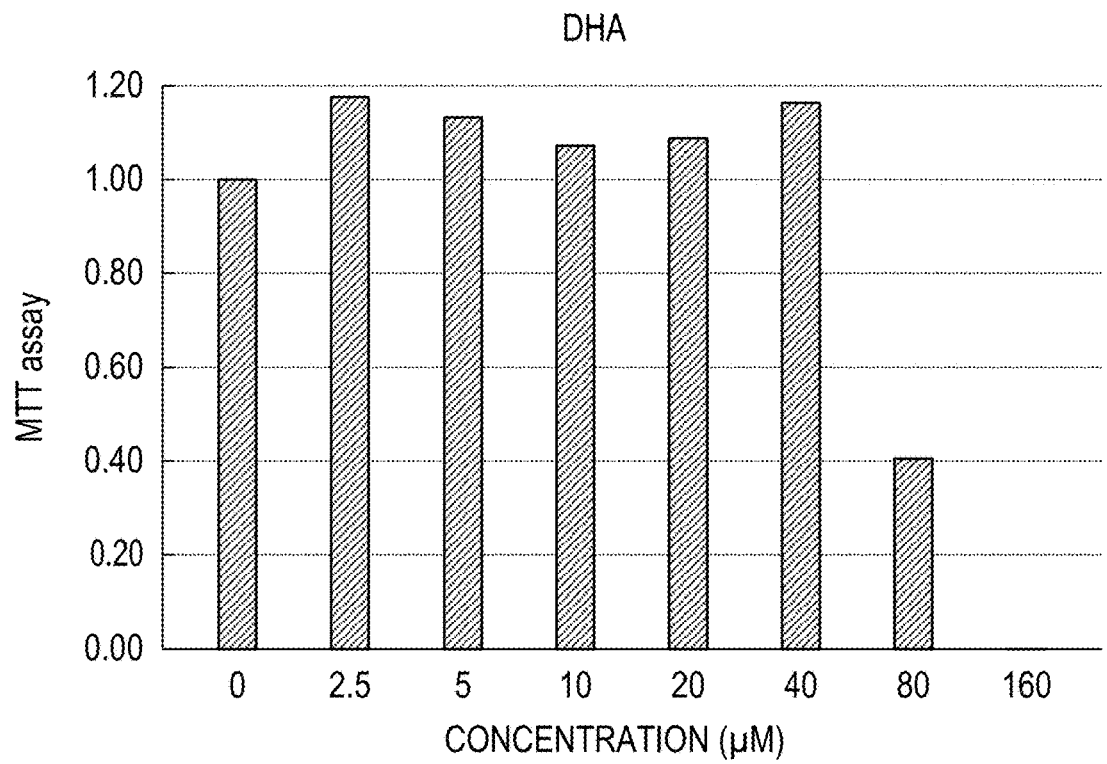
FIG. 10 is a diagram showing results of a toxicity test of DHA according to Experimental example 4.
Figure 11:
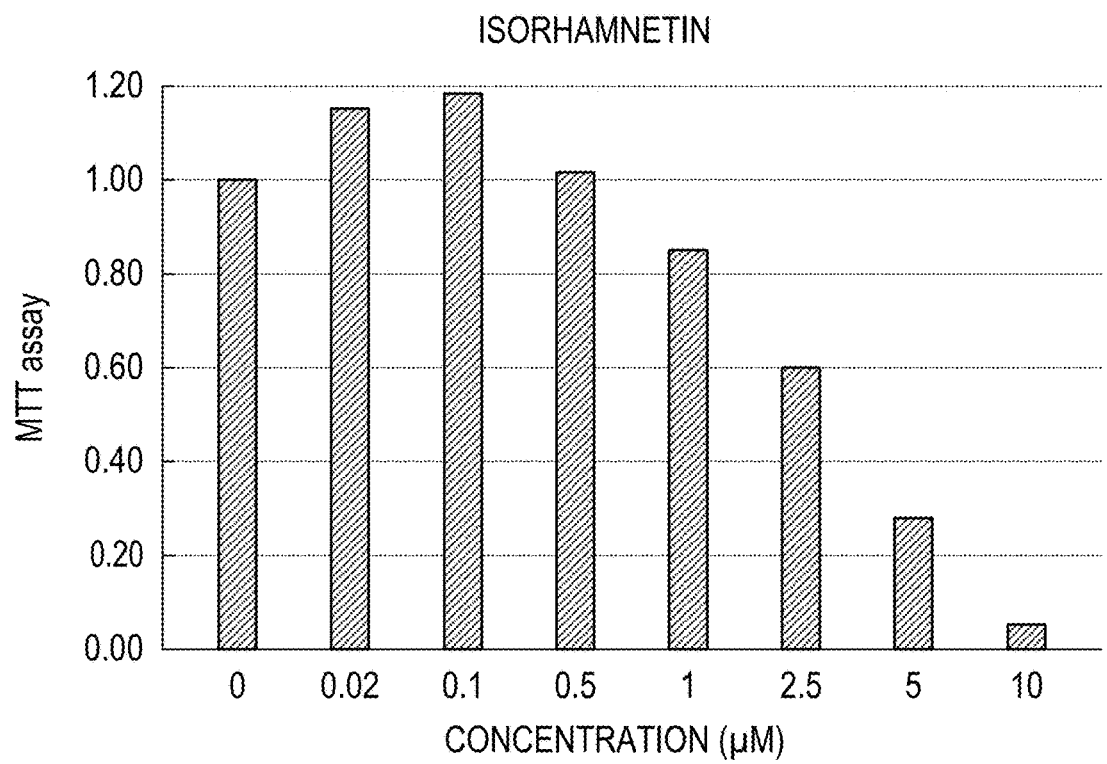
FIG. 11 is a diagram showing results of a toxicity test of isorhamnetin according to Experimental example 4.

After culturing in the above step (4), the plate was centrifuged to allow the cells to settle in the wells. Supernatants were removed. Three microscopic images (bright field, ×10 images, three wells per well) of PC12 cells settled in each well were taken. The shape of the whole PC12 cells in the images was observed. A shown in FIG. 6, when PC12 cells undergo differentiation, a neurite 2 extends from a cell body 1. The total number of PC12 cells, and the number of cells having the neurite 2 with a length L2 were counted. The length L2 is a longer length than a longer diameter L1 of the cell body 1. The number of cells having the neurite with the length L2 was divided by the total number of cells to obtain an extension percentage of the PC12 cells. In each image, at least 80 PC12 cells appeared. The total number of the PC12 cells appearing in all images was 720 or more. The extension percentage was expressed by an average value of all PC12 cells appearing in all images. The extension percentage of each PC12 cell was shown in FIG. 7. In FIG. 7, "M", "C", "D", and "I" sequentially mean "6-MSITC", "curcumin", "DHA", and "isorhamnetin". The same applies to FIGS. 8 to 11. In FIG. 7, τ means statistically significant. * means that synergistic effect was confirmed by combining two components. Synergistic effect herein means that use of two components in combination can increase the extension percentage as compared to a sum of extension percentages when each component is used alone.

As shown in FIG. 7, neurite extension effect was enhanced by containing any one of 6-MSITC, curcumin, DHA, and isorhamnetin in the medium, as compared to a case without these components. Neurite extension effect of 6-MSITC was higher than those of curcumin, DHA, and isorhamnetin.

When 0.1 μM, 0.5 μM, or 2.5 μM of 6-MSITC was added to the medium, significant extension enhancement was observed for PC12 cells. When 0.1 μM, 0.5 μM, or 2.5 μM of curcumin was added to the medium, significant extension enhancement was observed for PC12 cells. When 0.5 μM, 2.5 μM, or 40 μM of DHA was added to the medium, significant extension enhancement was observed for PC12 cells. When 0.02 μM, 0.1 μM, or 0.5 μM of isorhamnetin was added to the medium, significant extension enhancement was observed for PC12 cells.

As compared to the case of using only one type of component, the extension percentage was higher when two types including 6-MSITC and the other component are combined. In combination of 6-MSITC and curcumin, the extension percentage effectively increased when 6-MSITC is 0.1 to 2.5 μM and curcumin is 0.1 to 2.5 μM. In combination of 6-MSITC and DHA, the extension percentage effectively increased when 6-MSITC is 0.1 to 2.5 μM and DHA is 0.5 to 40 μM. In combination of 6-MSITC and isorhamnetin, the extension percentage effectively increased when 6-MSITC is 0.1 μM and 2.5 μM and isorhamnetin is 0.02 to 0.5 μM.

Experimental Example 4

Toxicity of each component to PC12 cells was investigated using an MTT (3-(4,5-di-methylthiazol-2-yl)-2,5-diphenyltetrazolium bromide, yellow tetrazole) reagent.

In order to investigate toxicity of each component to PC12 cells, the PC12 cells were cultured in the same manner as in the above steps (1) to (4) of Experimental example 3, except for components added to the medium. The component added to the differentiation medium B in each well in the above step (4) is any one of 6-MSITC (Component 1), curcumin (Component 3), DHA (Component 2), or isorhamnetin (Component 4). Concentrations of the respective components in the differentiation medium B were 0 (control), 2.5 μM, 5 μM, 10 μM, 20 μM, 40 μM, 80 μM, and 160 μM with respect to 6-MSITC (Component 1), 0 (control), 2.5 μM, 5 μM, 10 μM, 20 μM, and 40 μM with respect to curcumin (Component 3), 0 (control), 2.5 μM, 5 μM, 10 μM, 20 μM, 40 μM, 80 μM, and 160 μM with respect to DHA (Component 2), and 0 (control), 2.5 μM, 5 μM, 10 μM, and 20 μM with respect to isorhamnetin (Component 4).

After the PC12 cells were cultured for 72 hours in the above step (4) PC12 cell differentiation of Experimental example 3, 10 μl/well of MTT reagent (manufactured by Nacalai Tesque, Inc., Product No. 23547-21, MTT 5 mg/ml in a phosphate buffered saline) was added. Further, the plate was placed in a carbon dioxide incubator (5% $CO_2$, 37° C.), and the PC12 cells were cultured for 4 hours.

The plate was centrifuged to allow the cells to settle in the wells. Supernatants were removed. To each well, 100 μl/well of DMSO was added, shaken and stirred to suspend the PC12 wells in DMSO to obtain a cell solution.

Absorbance of 490 nm was measured for the cell solution in each well. A fraction, of which denominator is absorbance of the cell solution of the control and numerator is absorbance of the cell solution of PC12 cells cultured in the culture medium including each sample, is converted into a decimal number, and a resulting value was shown as an MTT assay. Results of measurements in case of using 6-MSITC, curcumin, DHA, and isorhamnetin are sequentially shown in FIGS. 8, 9, 10, and 11.

In case of using 6-MSITC, curcumin, DHA, and isorhamnetin, the MTT assay was higher than the case of not using them (control). In view of the above, it was found that toxicity of 6-MSITC, curcumin, DHA, and isorhamnetin is low.

Experimental Example 5

Resistance Test of Neurons Against Amyloid β

The above steps (1) Preparation of various components and (2) Preparation of media in Experimental example 1 were carried out to prepare (a) 6-MSITC (Component 1), (b) DHA (Component 2), (c) curcumin (Component 3), the growth medium A and the differentiation medium B.

(3) PC12 Cell Proliferation

The above growth medium A was added to a flask for cell culture (manufactured by TPP), and PC12 cells (manufactured by RIKEN, Product No. RCB0009) were further added for growth. PC12 cells are pheochromocytomas derived from rat's adrenal medulla, and are models of neuronnal differentiation. When PC12 cells reached confluence of 80-90%, the grown PC12 cells were seeded in a new flask containing the growth medium A and subcultured. A ratio of the culture medium with the grown cells to the new growth medium A was 1:5 (volume ratio). Such passage was repeated at least three times.

(4) PC12 Cell Differentiation

In each well of a 96-well plate, 100 μl of growth medium A containing the post-passage PC12 cells obtained in the above step (3) at a concentration of $5 \times 10^4$/ml was seeded. The plate was left overnight at room temperature so as to stabilize the PC12 cells. The plate was centrifuged and the PC12 cells were allowed to settle in each well of the plate. Supernatants were removed. To each well in which the PC12 cells were settled, 100 μl of differentiation medium B was added and stirred, so as to suspend the PC12 cells in the differentiation medium B.

To the medium in each well, NGF (manufactured by Sigma-Aldrich, Product No. N2513) was added. A concentration of NGF contained in the medium in all wells was 50 ng/ml. The well plate was placed in a carbon dioxide incubator (5% $CO_2$, 37° C.), and the PC12 cells were cultured for 72 hours.

Each of the components 1 to 4 prepared in the above step (1) of Experimental example 1 was added to the medium in each well so as to achieve various concentrations in one kind or in combination of two kinds. Each sample is numbered 1 to 38. The differentiation medium B was used for concentration adjustment. Table 3 shows concentrations of the components contained in each sample in the medium in each well. Further, amyloid β (manufactured by Ana Spec, Inc., Item No. AS-24224) was added to the medium in each well. A concentration of amyloid β in the medium is 1 μmol/L. In addition to the above samples, a sample in which neither the components 1 to 4 nor amyloid β was added to the medium was referred to as "control". Also, a sample in which amyloid β was added to the medium but the components 1 to 4 were not was referred to as "AMB".

Thereafter, the well plate was placed in a carbon dioxide incubator (5% $CO_2$, 37° C.), and the PC12 cells were cultured for 24 hours.

TABLE 3

(Unit: μM)

| Sample | 6-MSITC | curcumin | DHA | isorhamnetin |
|---|---|---|---|---|
| Control (amyloid β not added) | | | | |
| AMB | | | | |
| 1 | 0.1 | | | |
| 2 | 0.5 | | | |
| 3 | 2.5 | | | |
| 4 | | 0.1 | | |
| 5 | | 0.5 | | |
| 6 | | 2.5 | | |
| 7 | | | 0.5 | |
| 8 | | | 2.5 | |
| 9 | | | | 0.02 |
| 10 | | | | 0.1 |
| 11 | | | | 0.5 |
| 12 | 0.1 | 0.1 | | |
| 13 | 0.1 | 0.5 | | |
| 14 | 0.1 | 2.5 | | |
| 15 | 0.5 | 0.1 | | |
| 16 | 0.5 | 0.5 | | |
| 17 | 0.5 | 2.5 | | |
| 18 | 2.5 | 0.1 | | |
| 19 | 2.5 | 0.5 | | |
| 20 | 2.5 | 2.5 | | |
| 21 | 0.1 | | 0.5 | |
| 22 | 0.1 | | 2.5 | |
| 23 | 0.1 | | 40 | |
| 24 | 0.5 | | 0.5 | |
| 25 | 0.5 | | 2.5 | |
| 26 | 0.5 | | 40 | |
| 27 | 2.5 | | 0.5 | |
| 28 | 2.5 | | 2.5 | |
| 29 | 2.5 | | 40 | |
| 30 | 0.1 | | | 0.02 |
| 31 | 0.1 | | | 0.1 |
| 32 | 0.1 | | | 0.5 |
| 33 | 0.5 | | | 0.02 |
| 34 | 0.5 | | | 0.1 |
| 35 | 0.5 | | | 0.5 |
| 36 | 2.5 | | | 0.02 |
| 37 | 2.5 | | | 0.1 |
| 38 | 2.5 | | | 0.5 |

(5) Amyloid β Neurotoxicity Resistance Test

Resistance of PC12 cells to amyloid β was investigated using an MTT (3-(4,5-di-methylthiazol-2-yl)-2,5-diphenyltetrazolium bromide, yellow tetrazole) reagent.

10 μl/well of MTT reagent (manufactured by Nacalai Tesque, Inc., Product No. 23547-21, MTT 5 mg/ml in phosphate buffered saline) was added after the above step (4) PC12 cell differentiation. Further, the plate was placed in a carbon dioxide incubator (5% $CO_2$, 37° C.), and the PC12 cells were cultured for 4 hours.

The plate was centrifuged to allow the cells to settle in the wells. Supernatants were removed. To each well, 100 μl/well of DMSO was added, shaken and stirred to suspend the PC12 wells in DMSO to obtain a cell solution.

Absorbance of 490 nm was measured for the cell solution in each well. A fraction, of which denominator is absorbance of the cell solution of the control and numerator is absorbance of the cell solution of PC12 cells cultured in the culture medium including each sample, was converted into a decimal number, and a resulting value was shown as an MTT assay. Results of measurements are shown in FIG. 12.

Figure 12:
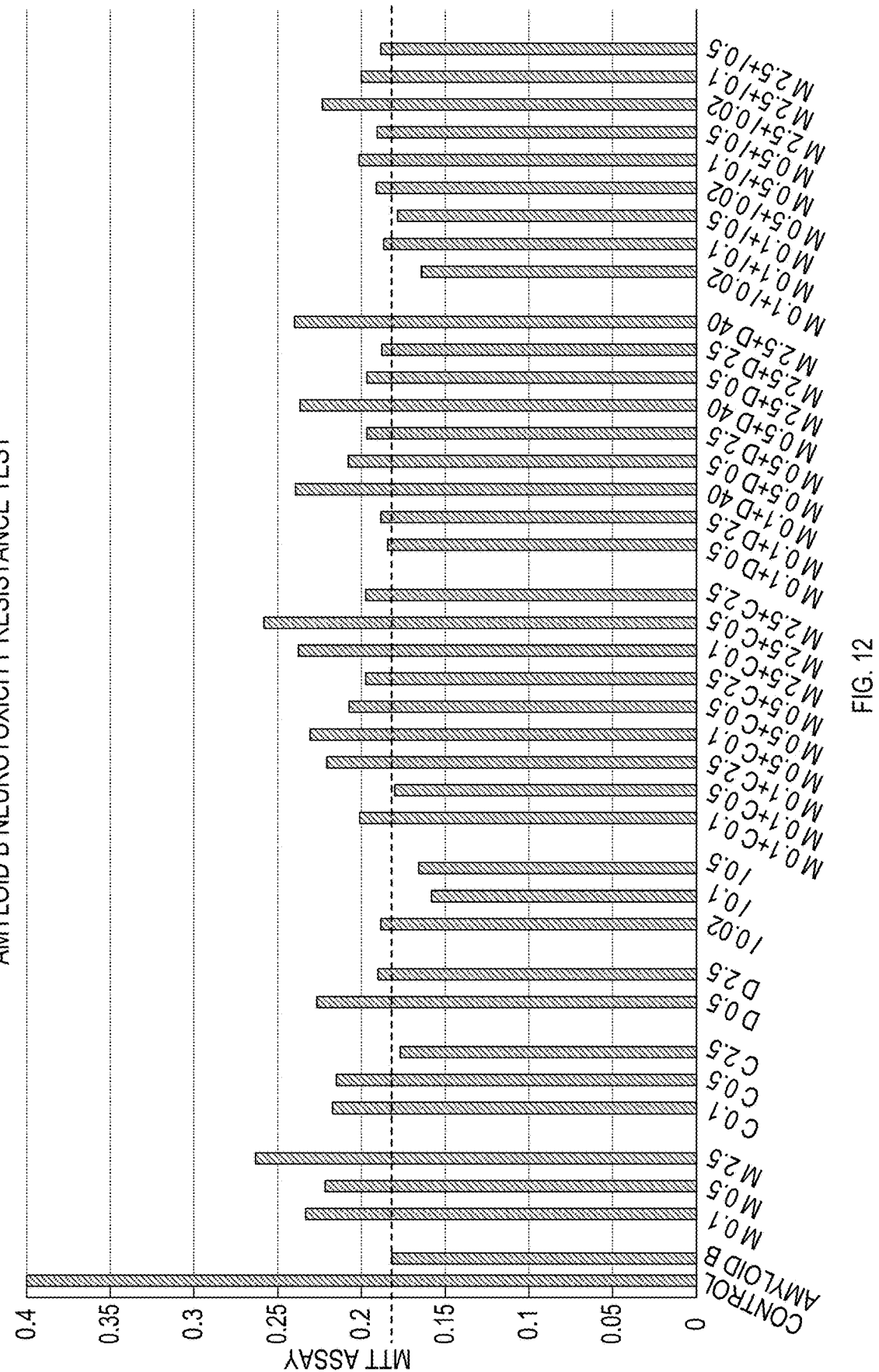
FIG. 12 is a diagram showing results of an amyloid $\beta$ neurotoxicity resistance test according to Experimental example 5.

In FIG. 12, "M", "C", "D", and "I" sequentially mean "6-MSITC", "curcumin", "DHA", and "isorhamnetin". The same applies to FIG. 13.

As shown in FIG. 12, as compared to the case of the medium without amyloid β (control), the MTT assay significantly decreased when the PC12 cells were cultured in the medium containing only amyloid β (AMB). The effect of enhancing amyloid β resistance of PC12 cells by 6-MSITC was higher than those of curcumin, DHA, and isorhamnetin. As compared to the case of culturing the cells in the medium containing only amyloid β (AMB), the MTT assay was higher when 6-MSITC was combined with curcumin, DHA or isorhamnetin and added to the medium together with amyloid β.

Experimental Example 6

Resistance Test of Neurons Against Hydrogen Peroxide

In Experimental example 6, resistance of PC12 cells against hydrogen peroxide was tested. The test method is the same as that of Experimental example 5, except that hydrogen peroxide was added to the differentiation medium B, instead of amyloid β in Experimental example 5 above. A concentration of hydrogen peroxide in the differentiation medium B was 100 μM. Results of the experiment were shown in FIG. 13.

Figure 13:
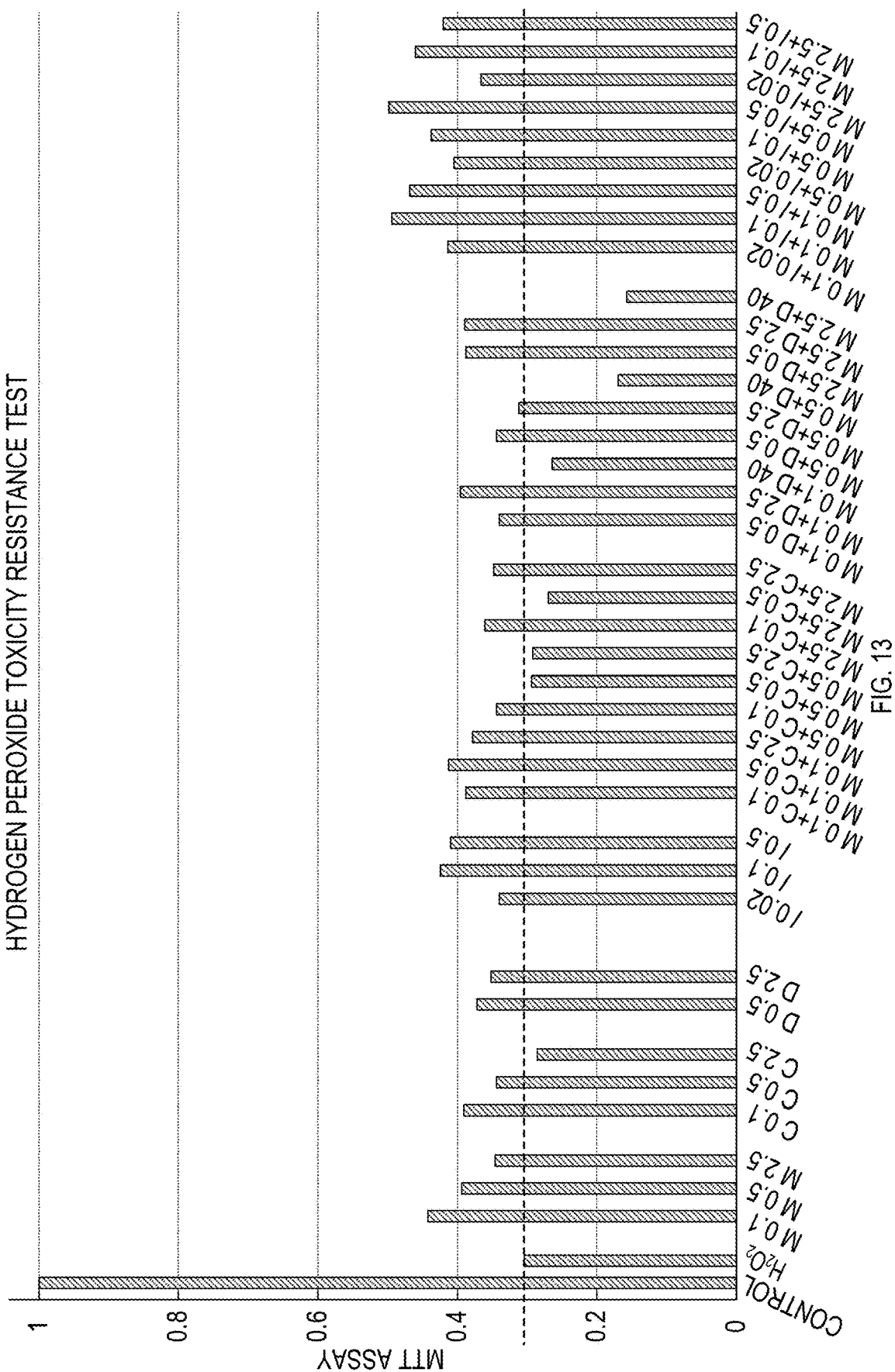
FIG. 13 is a diagram showing results of a hydrogen peroxide toxicity resistance test according to Experimental example 6.

As shown in FIG. 13, as compared to a case of culturing in the medium without hydrogen peroxide (control), the MTT assay significantly decreased when the PC12 cells were cultured in the medium containing only hydrogen peroxide ($H_2O_2$). When 6-MSITC, curcumin, DHA or isorhamnetin was added alone, or when a combination of 6-MSITC and curcumin, DHA or isorhamnetin was added to the medium, the MTT assay showed a value without problem.

In view of the above experiments, it was confirmed that there is a function of protecting neurons against internally produced amyloid β and hydrogen peroxide when 6-MSITC and curcumin, DHA, or isorhamnetin are combined, as compared to the case without these components and the case in which these components are used alone.

The influence of amyloid β on neurons is considered to be related to reactive oxygen species. Reactive oxygen species are known to take various forms such as single oxygen, hydrogen peroxide, lipid peroxide and the like due to its high reactivity, and increase damage to cells. Having resistance against both amyloid β and hydrogen peroxide is useful since there is a possibility that disorders by these various active oxygen species can be widely inhibited.

What is claimed is:

1. A method of activating neurons by promoting dopamine production of the neurons, promoting extension of the neurons, or enhancing resistance of the neurons against amyloid β,
    comprising administering an effective amount of a neuron activator to a subject in need thereof,
    the neuron activator including
        6-methylsulfinylhexyl isothiocyanates or glycosides thereof, and
        at least one selected from the group consisting of unsaturated fatty acid and polyphenol.

2. The method according to claim 1, wherein the unsaturated fatty acid includes ω-3 fatty acid.

3. The method according to claim 2, wherein the ω-3 fatty acid includes at least one selected from the group consisting of docosahexaenoic acid and eicosapentaenoic acid.

4. The method according to claim 2, wherein the ω-3 fatty acid is extracted from fish and shellfish and/or fish oil.

5. The method according to claim 1, wherein the polyphenol includes at least one selected from the group consisting of curcuminoid and flavonoid.

6. The method according to claim 5, wherein the curcuminoid includes curcumin.

7. The method according to claim 5, wherein the curcuminoid is extracted from turmeric.

8. The method according to claim 5, wherein the flavonoid includes isorhamnetin.

\* \* \* \* \*